United States Patent
Abdi

(10) Patent No.: US 12,180,286 B2
(45) Date of Patent: *Dec. 31, 2024

(54) ANTI-PERIPHERAL LYMPH NODE ADDRESSIN ANTIBODIES AND USES THEREOF

(71) Applicant: The Brigham and Women's Hospital, Inc., Boston, MA (US)

(72) Inventor: Reza Abdi, Newton, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/334,499

(22) Filed: May 28, 2021

(65) Prior Publication Data
US 2021/0284740 A1 Sep. 16, 2021

Related U.S. Application Data

(63) Continuation of application No. 16/788,773, filed on Feb. 12, 2020, now Pat. No. 11,028,176.

(60) Provisional application No. 62/804,797, filed on Feb. 13, 2019.

(51) Int. Cl.
*C07K 16/28* (2006.01)
*A61K 47/65* (2017.01)
*A61P 35/00* (2006.01)
*C07K 16/30* (2006.01)

(52) U.S. Cl.
CPC .......... *C07K 16/2854* (2013.01); *A61K 47/65* (2017.08); *A61P 35/00* (2018.01); *C07K 16/30* (2013.01)

(58) Field of Classification Search
None
See application file for complete search history.

(56) References Cited

U.S. PATENT DOCUMENTS

| | | | | |
|---|---|---|---|---|
| 5,538,724 A * | 7/1996 | Butcher | ............ | C07K 16/2884 424/143.1 |
| 6,180,370 B1 * | 1/2001 | Queen | ............. | A61P 19/02 435/69.6 |
| 10,898,581 B2 * | 1/2021 | Abdi | ............. | A61K 47/6849 |
| 11,028,176 B2 | 6/2021 | Abdi | | |
| 2007/0059240 A1 | 3/2007 | Baddoura | | |
| 2013/0101504 A1 | 4/2013 | Trieu et al. | | |
| 2016/0068596 A1 | 3/2016 | de Sauvage et al. | | |
| 2016/0331843 A1 * | 11/2016 | Abdi | ............. | A61K 47/6849 |
| 2020/0255532 A1 | 8/2020 | Abdi | | |

FOREIGN PATENT DOCUMENTS

| CN | 101583626 A | 11/2009 |
|---|---|---|
| JP | 2011512332 A | 4/2011 |
| JP | 2018508215 A | 3/2018 |
| WO | WO 2015/108783 | 7/2015 |
| WO | WO 2018/191548 | 10/2018 |

OTHER PUBLICATIONS

Rosen, Steven D et al. The American journal of pathology vol. 166,3 (2005): 935-44. doi: 10.1016/S0002-9440(10)62313-9 (Year: 2005).*
Xu, Baohui, Rachel E. Cook, and Sara A. Michie. Journal of autoimmunity 35.2 (2010): 124-129 (Year: 2010).*
Mekhail, Tarek M, and Maurie Markman. Expert opinion on pharmacotherapy vol. 3,6 (2002): 755-66. doi: 10.1517/14656566.3.6.755 (Year: 2002).*
"Immunosuppression" National Cancer Institute. Published Apr. 29, 2015. https://www.cancer.gov/about-cancer/causes-prevention/risk/immunosuppression (Year: 2015).*
Kipriyanov, Sergey M., and Fabrice Le Gall. "Generation and production of engineered antibodies." Molecular biotechnology 26.1 ( 2004): 39-60. (Year: 2004).*
Janeway, Charles A. "Immunobiology: The Immune System in Health and Disease." 2001 (Year: 2001).*
Andrian & MacKay., "T-cell function and migration—two sides of the same coin," N. Engl. J. Med., Oct. 2000, 343(14):1020-1034.
Dong et al., "Vascular addressins in the uterus and pancreas of type 1 diabetic mice in early pregnancy," Placenta, Feb. 2008, 29(2):201-209.
Faveeuw et al., "Expression of homing and adhesion molecules in infiltrated islets of Langerhans and salivary glands of nonobese diabetic mice," J. Immunol., Jun. 1994, 152(12):5969-5978.
Faveeuw et al., "Homing of lymphocytes into islets of Langerhans in prediabetic non-obese diabetic mice is not restricted to autoreactive T cells," Int. Immunol., Dec. 1995, 7(12):1905-1913.
Hanninen et al., "Mucosa-Associated (βT-integrin high) Lymphocytes Accumulate Early in the Pancreas of NOD Mice and Show Aberrant Recirculation Behavior," Diabetes, Sep. 1996, 45(9):1173-1180.
Hanninen et al., "Recirculation and homing of lymphocyte subsets: dual homing specificity of beta 7-integrin (high)-lymphocytes in nonobese diabetic mice," Blood, Aug. 1996, 88(3):934-944.

(Continued)

*Primary Examiner* — Michael Szperka
*Assistant Examiner* — Lia E Taylor
(74) *Attorney, Agent, or Firm* — Fish & Richardson P.C.

(57) ABSTRACT

The present disclosure provides, inter alia, anti-peripheral lymph node addressin antibodies and antigen binding fragments thereof. The present disclosure also provides compositions comprising drug-containing polymeric particles that mimic lymphocyte migration in vivo and can specifically deliver immunosuppressive or immunoregulatory drugs to lymphoid tissues and sites of chronic inflammation where T-cell activation and T-cell mediated injury are occurring; such compositions comprise the antibodies or antigen-binding fragments thereof described in the disclosure. The present disclosure also comprises antibody-drug conjugates and compositions comprising the antibody-drug conjugates. Methods of preparing and using these antibodies, antigen-binding fragments thereof, and compositions thereof are also provided.

15 Claims, 11 Drawing Sheets

Specification includes a Sequence Listing.

(56) References Cited

OTHER PUBLICATIONS

Hemmerich et al., "Sulfation-dependent recognition of high endothelial venules (HEV)-ligands by L-selectin and MECA 79, and adhesion-blocking monoclonal antibody," J. Exp. Med., Dec. 1994, 180(6):2219-2226.

Hirakawa et al., "Novel Anti-carbohydrate Antibodies Reveal the Cooperative Function of Sulfated N- and O-Glycans in Lymphocyte Homing," J Biol Chem, Dec. 2010, 285(52):40864-40878.

Hoglund et al., "Initiation of autoimmune diabetes by developmentally regulated presentation of islet cell antigens in the pancreatic lymph nodes," J. Exp. Med., Jan. 1999, 189(2):331-339.

Huston et al., "Protein engineering of antibody binding sites: recovery of specific activity in an anti-digoxin single-chain Fv analogue produced in *Escherichia coli*," PNAS, Aug. 1988, 85(16):5879-5883.

Janeway, A. C., et al. "Immunobiology: the immune system in health and disease. London." Current Biology (1997): 3:1-3:11. (Year: 1997).

Katz et al., "Following a diabetogenic T cell from genesis through pathogenesis," Cell, Sep. 1993, 74(6):1089-1100.

Liu et al., "Expression of MAdCAM-1 and PNAd in inflammatory and MALT lymphoma tissues of ocular adnexa, thyroid, salivary gland and lung," Clin. Exp. Hematopathol., Apr. 2004, 44(1):33-37.

Mackay., "Moving targets: cell migration inhibitors as new anti-inflammatory therapies," Nat. Immunol., Sep. 2008, 9(9):988-998.

Michie et al., "The human peripheral lymph node vascular addressin. An inducible endothelial antigen involved in lymphocyte homing." Am. J. Pathol., Dec. 1993, 143(6):1688-1698.

Mikulowska-Mennis et al., "Lymphocyte migration to inflamed lacrimal glands is mediated by vascular cell adhesion molecule-1/ α4β1 integrin, peripheral node addressin/l-selectin, and lymphocyte function-associated antigen-1 adhesion pathways," Am. J. Pathol., Aug. 2001, 159(2):671-681.

Pals et al., "Lymphoma dissemination: the other face of lymphocyte homing, " Blood, Nov. 2007, 110(9):3102-3111.

PCT International Preliminary Report on Patentability in International Appln. No. PCT/US2020/017879, dated Aug. 26, 2021, 7 pages.

PCT International Search Report and Written Opinion in International Appln. No. PCT/US2020/017879, dated May 20, 2020, 10 pages.

Penaranda & Bluestone, "Is antigen specificity of autoreactive T cells the key to islet entry?," Immunity, Oct. 2009, 31(4):534-536.

Roncarolo & Battaglia, "Regulatory T-cell immunotherapy for tolerance to self-antigens and alloantigens in humans," Nat. Rev. Immunol., Aug. 2007, 7(8):585-598.

Rudikoff et al. "K Chain joining segments and structural diversity of antibody combining sites," Proceedings of the National Academy of Sciences USA, Jul. 1980, 77(7):4270-4274.

Streeter et al., "Immunohistologic and functional characterization of a vascular addressin involved in lymphocyte homing into peripheral lymph nodes," J. Cell. Biol., Nov. 1998, 107(5):1853-1862.

Turley et al., "Physiological β cell death triggers priming of self-reactive T cells by dendritic cells in a type-1 diabetes model," J. Exp. Med., Nov. 2003, 198(10):1527-1537.

Xu et al., "Lymphocyte homing to bronchus-associated lymphoid tissue (BALT) is mediated by L-selectin/PNAd, α4β1 integrin/ VCAM-1, and LFA-1 adhesion pathways," J. Exp. Med., May 2003, 197(10):1255-1267.

Xu et al., "α4β7 integrin/MAdCAM-1 adhesion pathway is crucial for B cell migration into pancreatic lymph nodes in nonobese diabetic mice," J. Autoimmune., Sep. 2010, 35(2):124-129.

Yang et al., "A predominant role of integrin alpha 4 in the spontaneous development of autoimmune diabetes in nonobese diabetic mice," Proc. Natl. Acad. Sci. USA, Dec. 1994, 91(26):12604-12608.

Yang et al., "Cell adhesion molecules: a selective therapeutic target for alleviation of IDDM," J. Autoimmune., Dec. 1994, 7(6):859-864.

Azzi et al., "Targeted delivery of immunomodulators to lymph nodes," Cell Reports, May 10, 2016, 15(6):1202-13.

Kawashima et al., "Sulfated glycans control lymphocyte homing," Annals of the New York Academy of Sciences, Apr. 2012, 1253(1):112-21.

CN Office Action in Chinese Appln. No. 202080028019.0, mailed on Mar. 15, 2024, 9 pages (with English translation).

Han et al., "Class switch recombination and somatic hypermutation in early mouse B cells are mediated by B cell and Toll-like receptors," Immunity, Jul. 2007, 27(1):64-75.

Jiang et al., "Simultaneous targeting of primary tumor, draining lymph node, and distant metastases through high endothelial venule-targeted delivery," Nano Today, Feb. 2021, 36:101045, 36 pages.

JP Office Action in Japanese Appln. No. 2021547170, mailed on Jan. 30, 2024, 53 pages (with English translation).

Kobayashi et al., "Prominent expression of sialyl Lewis X-capped core 2-branched O-glycans on high endothelial venule-like vessels in gastric MALT lymphoma," The Journal of Pathology, May 2011, 224(1):67, 21 pages.

Von Andrian and Mackay, "T-cell function and migration—two sides of the same coin," New England journal of Medicine, Oct. 2000, 343(14):1020-1034.

* cited by examiner

FIG. 5

| | FR1 | CDR1 | FR2 | CDR2 | FR3 | CDR3 | FR4 |
|---|---|---|---|---|---|---|---|
| MHA112 VH | QVQLKESGPGLVAPSQSLSITCTVS | GFSLTSY | GVDWVRQPPGKGLEWLGVI | WGGGS | TNYNSALMSRLSISKDNSKSQ VFLKMNSLQTDDTAMYYCAK | HSKGGYFDV | WGTGTTVTVSS |
| MHA112 VL | EIVLTQSPAITAASLGQKVTITC | SASSSVSYMH | WYQQKSGTSPKPWIY | EISKLAS | GVPARFSGSGSGTSYSLTISSM EAEDAAIYYC | QQWNYPLIT | FGAGTKLELK |

ANTI-PERIPHERAL LYMPH NODE ADDRESSIN ANTIBODIES AND USES THEREOF

CLAIM OF PRIORITY

This application is a continuation of U.S. patent application Ser. No. 16/788,773, filed Feb. 12, 2020, which claims the benefit of U.S. Provisional Patent Application Ser. No. 62/804,797, filed on Feb. 13, 2019. The entire contents of the foregoing are hereby incorporated by reference.

SEQUENCE LISTING

The instant application contains a Sequence Listing which has been submitted electronically in ASCII format and is hereby incorporated by reference in its entirety. Said ASCII copy, created on Apr. 27, 2021, is named "Sequence Listing" and is 7,333 bytes in size.

TECHNICAL FIELD

This invention relates to anti-peripheral lymph node addressin (PNAd) antibodies, antigen-binding fragments thereof, and conjugates thereof, and uses thereof.

BACKGROUND

The peripheral lymph node addressin (PNAd) is a tissue-specific endothelial cell antigen constitutively expressed on high endothelial venules (HEV) in both mouse and human. PNAds are a group of endothelial sialomucins—CD34, podocalixin, glycosylation-dependent cell-adhesion molecule 1 (GlyCAM-1), and sialylated glycoprotein of 200 kDa (sgp200)—all of which include a sulfated sialyl-LewisX (sLeX)-like motif (von Andrian, U. H. & Mackay, C. R., N Engl J Med 343: 1020-1034, 2000). PNAds are expressed on venular endothelium of peripheral lymph nodes, tonsils, almost all the sites of inflammation or lymphomatous lesions, but not in normal tissues of the ocular adnexa, thyroid gland, salivary gland and lung (Liu Y, J Clin Exp Hematopathol 44 (1): 33-37, 2004). PNAds play important roles in lymphocyte homing to the inflamed lesions and in biological behavior of lymphoma cells in MALT lymphoma tissues of these organs.

Inflammation is a key pathogenic process in a very large number of prevalent diseases from classical immune-mediated diseases such as rheumatoid arthritis to cancer. From graft rejection where leukocytes invade the transplanted organ, to multiple sclerosis where lymphocytes invade brain to atherosclerotic plaque where leukocytes aggravate lipid induced micro and macro-vascular injuries, immune or inflammatory responses are central to the development of these diseases. The past decade has witnessed major advancements in the development of new immunosuppressive drugs. These drugs have played a pivotal role in ensuring the success of organ transplantation and have greatly improved the outcomes of patients with life-threatening, immune-mediated diseases. However, the use of immunosuppressive agents is hindered by the lack of selectivity and frequently observed major adverse drug reactions.

SUMMARY

The present disclosure provides an anti-peripheral lymph node addressin (PNAd) antibody, or a PNAd-binding fragment thereof, and methods of using same.

In one aspect, the disclosure features an anti-peripheral lymph node addressin (PNAd) antibody, or a PNAd-binding fragment thereof, comprising: (a) a heavy chain variable region (VH), wherein the VH comprises a VH complementarity determining region 1 (CDR1) comprising the amino acid sequence of SEQ ID NO:3, a VH CDR2 comprising the amino acid sequence of SEQ ID NO:4, and a VH CDR3 comprising the amino acid sequence of SEQ ID NO:5; and (b) a light chain variable region (VL), wherein the VL comprises a VL CDR1 comprising the amino acid sequence of SEQ ID NO:8, a VL CDR2 comprising the amino acid sequence of SEQ ID NO:9, and a VL CDR3 comprising the amino acid sequence of SEQ ID NO:10.

In some embodiments, the VH comprises a VH framework region 1 (FR1) comprising the amino acid sequence set forth in SEQ ID NO:11, a VH FR2 comprising the amino acid sequence set forth in SEQ ID NO:12, a VH FR3 comprising the amino acid sequence set forth in SEQ ID NO:13, and a VH FR4 comprising the amino acid sequence set forth in SEQ ID NO:14.

In some embodiments, the VL comprises a VL FR1 comprising the amino acid sequence set forth in SEQ ID NO:15, a VL FR2 comprising the amino acid sequence set forth in SEQ ID NO:16, a VL FR3 comprising the amino acid sequence set forth in SEQ ID NO:17, and a VL FR4 comprising the amino acid sequence set forth in SEQ ID NO:18.

In some embodiments, the VH comprises the amino acid sequence set forth in SEQ ID NO:2. In some embodiments, the VL comprises the amino acid sequence set forth in SEQ ID NO:7. In some embodiments, the VH comprises the amino acid sequence set forth in SEQ ID NO:2 and the VL comprises the amino acid sequence set forth in SEQ ID NO:7.

In some embodiments, the antibody is a monoclonal antibody. In some embodiments, the antibody is a murine antibody. In some embodiments, the antibody is a chimeric antibody. In some embodiments, the antibody is a humanized antibody.

In some embodiments, the antibody, or PNAd-binding fragment thereof, comprises human-derived heavy chain and light chain constant regions. In some embodiments, the antibody, or PNAd-binding fragment thereof, comprises a heavy chain constant region of isotype immunoglobulin mu (IgM).

In some embodiments, the PNAd-binding fragment is selected from the group consisting of a single chain Fv fragment (scFv), an F(ab') fragment, an F(ab) fragment, and an F(ab')2 fragment.

In some embodiments, the antibody, or PNAd-binding fragment thereof, is conjugated to an agent. In some embodiments, the agent is an imaging agent, a cytotoxic agent, or a drug. In some embodiments, the agent is a drug-containing polymeric particle. In some embodiments, the drug-containing polymeric particle comprises an immunosuppressive or immunoregulatory drug. In some embodiments, the conjugation to the agent is covalent conjugation. In some embodiments, the conjugation to the agent is via a linker. In some embodiments, the linker is polyethylene glycol.

Also provided herein are polynucleotides comprising nucleic acid sequences encoding the aforementioned antibody, or PNAd-binding fragment thereof.

Further provided herein are polynucleotides comprising nucleic acid sequences encoding a heavy chain variable region (VH), wherein the VH comprises the amino acid sequence set forth in SEQ ID NO:2. In some embodiments, the polynucleotide comprises the nucleic acid sequence set forth in SEQ ID NO:1. In some instances, the polynucleotide is operably linked to a promoter.

Additionally, provided herein are polynucleotides comprising nucleic acid sequences encoding a heavy chain, wherein the heavy chain comprises a heavy chain variable region (VH), wherein the VH comprises the amino acid sequence set forth in SEQ ID NO:2. In some embodiments, the polynucleotide comprises the nucleic acid sequence set forth in SEQ ID NO:1. In some instances, the polynucleotide is operably linked to a promoter.

Also provided herein are polynucleotides comprising nucleic acid sequences encoding a light chain variable region (VL), wherein the VL comprises the amino acid sequence set forth in SEQ ID NO:7. In some embodiments, the polynucleotide comprises the nucleic acid sequence set forth in SEQ ID NO:6. In some instances, the polynucleotide is operably linked to a promoter.

Also provided herein are polynucleotides comprising nucleic acid sequences encoding a light chain, wherein the light chain comprises a light chain variable region (VL), wherein the VL comprises the amino acid sequence set forth in SEQ ID NO:7. In some embodiments, the polynucleotide comprises the nucleic acid sequence set forth in SEQ ID NO:6. In some instances, the polynucleotide is operably linked to a promoter.

Also provided herein are vectors comprising a promoter operably linked to the aforementioned polynucleotide comprising nucleic acid sequences encoding: (i) a VH comprising the amino acid sequence set forth in SEQ ID NO:2 operably linked to a promoter; or (ii) a VL comprising the amino acid sequence set forth in SEQ ID NO:7.

Also provided herein are vectors comprising a promoter operably linked to the aforementioned polynucleotide comprising nucleic acid sequences encoding the heavy chain comprising the VH comprising the amino acid sequence set forth in SEQ ID NO:2.

Also provided herein are vectors comprising a promoter operably linked to the aforementioned polynucleotide comprising nucleic acid sequences encoding the light chain comprising the VL comprising the amino acid sequence set forth in SEQ ID NO:7.

Also provided herein are vectors comprising: (i) a first promoter operably linked to the aforementioned polynucleotide comprising nucleic acid sequences encoding the heavy chain comprising the VH comprising the amino acid sequence set forth in SEQ ID NO:2; and (ii) a second promoter operably linked to the aforementioned polynucleotide comprising nucleic acid sequences encoding the light chain comprising the VL comprising the amino acid sequence set forth in SEQ ID NO:7.

Also provided herein are host cells comprising one or more of the aforementioned polynucleotides operably linked to a promoter(s).

Also provided herein are host cells comprising one or more of the aforementioned vectors.

Also provided herein are methods of producing an anti-peripheral lymph node addressin (PNAd) antibody or PNAd-binding fragment thereof, comprising: (a) culturing an aforementioned host cell; and (b) isolating the antibody from the culture.

Also provided herein are pharmaceutical compositions comprising a therapeutically effective amount of the aforementioned antibody or PNAd-binding fragment thereof and a pharmaceutically acceptable carrier.

Also provided herein are methods of suppressing a lymphocyte-mediated immune response in a subject in need thereof, comprising administering to the subject a therapeutically effective amount of the aforementioned pharmaceutical composition.

Also provided herein are methods of treating or delaying progression of autoimmune diabetes in a subject in need thereof, administering to the subject a therapeutically effective amount of the aforementioned pharmaceutical composition.

Also provided herein are methods of treating lymphocyte-mediated inflammation in a subject in need thereof, the method comprising administering to the subject a therapeutically effective amount of the aforementioned pharmaceutical composition.

Also provided herein are methods of treating or reducing the metastasis of a peripheral lymph node addressin (PNAd)-expressing malignancy in a subject in need thereof, the method comprising administering to the subject a therapeutically effective amount of the aforementioned pharmaceutical composition. In some embodiments, the PNAd-expressing malignancy is lymphoma. In some embodiments, the PNAd-expressing malignancy is a cancer. In some instances, the cancer is breast cancer.

Also provided herein are methods of delivering a drug to a subject in need thereof, comprising administering to the subject a therapeutically effective amount of the aforementioned pharmaceutical composition, wherein the drug delivered to the subject is the drug of the drug-containing polymeric particle conjugated to the antibody or PNAd-binding fragment thereof of the pharmaceutical composition. In some embodiments, the drug is delivered to one or more lymphoid tissues or one or more sites of chronic inflammation in the subject.

The details of one or more embodiments of the invention are set forth in the accompanying drawings and the description below. Other features, objects, and advantages of the invention will be apparent from the description and drawings, and from the claims.

DESCRIPTION OF DRAWINGS

(FIG. 1A) Immunofluorescence staining showed low magnification image of HEVs staining by MHA112 mAb. Scale bar, 500 μm. (FIG. 1B) Immunofluorescence staining showed high magnification images of HEVs staining by MHA112 mAb in mice lymph nodes (LNs) and human tonsil. Scale bar, 100 μm.

(FIG. 3A) The fluorescent images showed the distribution of MHA112 mAb conjugated NP (MHA112-IR800-NPs) in different LNs. NPs only (IR800-NPs) was used as negative control and MECA79-NPs (MECA79 IR800-NPs) was used as positive control. (FIG. 3B) Immunofluorescence analysis of MECA79-NPs and MHA112-NPs distribution in Axillary LNs. HEVs was stained in green and IR800 dye in NPs was red. Scale bar, 50 μm.

FIG. 5: MHA112 sequence. The sequences of MHA112 heavy chain and light chain variable regions (VH and VL, respectively) are shown, with the framework regions (FR1-FR4) and IMGT complementarity determining regions (CDR1-CDR3) delineated. VH=SEQ ID NO:2; VH FR1-FR4=SEQ ID NOs:11-14, respectively; VH CDR1-3=SEQ ID NOs:3-5, respectively; VL=SEQ ID NO:7; VL FR1-FR4=SEQ ID NOs:15-18, respectively; VL CDR1-3=SEQ ID NOs:3-5, respectively.

DETAILED DESCRIPTION

I. Definitions

Figure 1B:
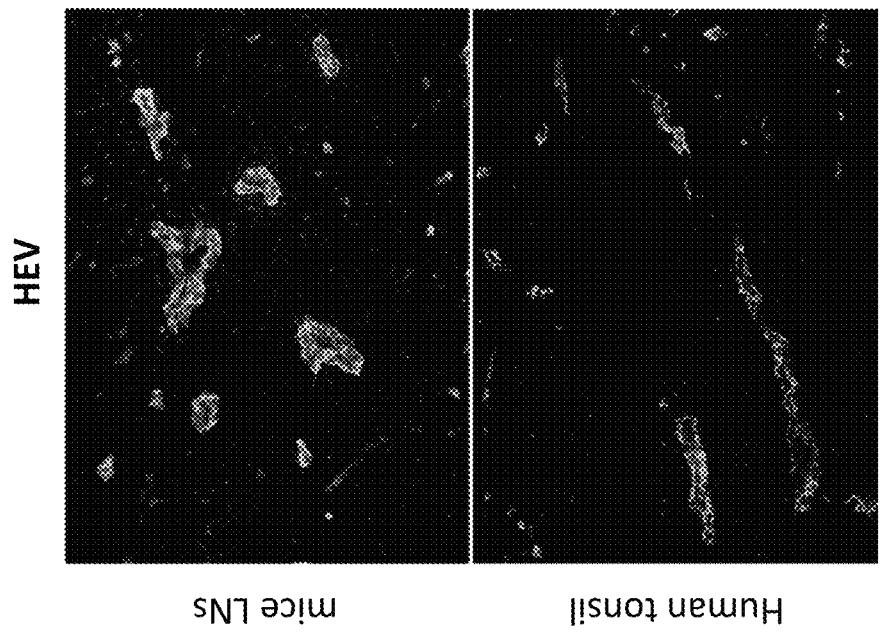
FIGS. 1A-B: MHA112 monoclonal antibody (mAb) recognizes high endothelial venules (HEVs) in mice and human.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide described herein may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposes described herein, as are native or recombinant polypeptides which have been separated, fractionated, or partially or substantially purified by any suitable technique.

Also included as polypeptides are fragments, derivatives, analogs or variants of the foregoing polypeptides, and any combination thereof. The terms "fragment," "variant," "derivative" and "analog" when referring to antibodies or antibody polypeptides described herein include any polypeptides which retain at least some of the antigen-binding properties of the corresponding native binding molecule, antibody, or polypeptide. Fragments of polypeptides described herein include proteolytic fragments, as well as deletion fragments, in addition to specific antibody fragments discussed elsewhere herein. Variants of antibodies and antibody polypeptides described herein include fragments as described above, and also polypeptides with altered amino acid sequences due to amino acid substitutions (e.g., conservative or non-conservative amino acid substitutions), deletions, or insertions. Variants may occur naturally or be non-naturally occurring. Non-naturally occurring variants may be produced using art-known mutagenesis techniques. Variant polypeptides may comprise conservative or non-conservative amino acid substitutions (e.g., conservative or non-conservative amino acid substitutions), deletions or additions. Derivatives of PNAd specific binding molecules, e.g., antibodies and antibody polypeptides described herein, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes described herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides described herein. Isolated polynucleotides or nucleic acids described herein further include such molecules produced synthetically. In addition, polynucleotide or a nucleic acid may be or may include a regulatory element such as a promoter, ribosome binding site, or a transcription terminator.

As used herein, a "coding region" is a portion of a nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions described herein can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid described herein may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In some embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In some embodiments, a polynucleotide described herein is RNA, for example, in the form of messenger RNA (mRNA).

Polynucleotide and nucleic acid coding regions described herein may be associated with additional coding regions that encode secretory or signal peptides, which direct the secretion of a polypeptide encoded by a polynucleotide described herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In some embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence can be substituted with the leader sequence of human tissue plasminogen activator (TPA) or mouse β-glucuronidase.

Unless stated otherwise, the terms "disorder" and "disease" are used interchangeably herein.

A "binding molecule" as used herein relates primarily to antibodies, and fragments thereof, but may also refer to other non-antibody molecules that bind to PNAd including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the disclosure most of the following embodiments are discussed with respect to antibodies and antibody-like molecules which represent a specific embodiment of binding molecules for the development of therapeutic and diagnostic agents.

The terms "antibody" and "immunoglobulin" are used interchangeably herein. An antibody or immunoglobulin is a PNAd-binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the disclosure. All immunoglobulin classes are clearly within the scope of the disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three-dimensional antigen-binding site. This quaternary antibody structure forms the antigen-binding site present at the end of each arm of the Y. More specifically, the antigen-binding site is defined by three CDRs on each of the VH and VL chains. Any antibody or immunoglobulin fragment that contains sufficient structure to specifically bind to PNAd is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof described herein are according to the Kabat numbering system, which however is theoretical and may not equally apply every antibody described herein. For example, depending on the position of the first CDR the following CDRs might be shifted in either direction.

Antibodies or antigen-binding fragments, immunospecific fragments, variants, or derivatives thereof described herein include, but are not limited to, polyclonal, monoclonal, multispecific, human, humanized, primatized, murinized or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules described herein can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In some embodiments, the antibody is not IgM or a derivative thereof with a pentavalent structure. Particular, in specific applications, especially therapeutic use, IgMs are less useful than IgG and other bivalent antibodies or corresponding binding molecules since IgMs due to their pentavalent structure and lack of affinity maturation often show unspecific cross-reactivities and very low affinity.

In some embodiments, the antibody is an IgM or a derivative thereof with a pentavalent structure.

In some embodiments, the antibody is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also provided herein are PNAd-binding fragments also comprising any combination of variable region(s) with a hinge region, CH1, CH2, and CH3 domains. Antibodies or immunospecific fragments thereof described herein may be from any animal origin including birds and mammals. In some embodiments, the antibodies are human, murine, donkey, rabbit, goat, guinea pig, camel, llama, horse, or chicken antibodies. In another embodiment, the variable region may be condricthoid in origin (e.g., from sharks).

In some embodiments, the antibody is a human monoclonal antibody isolated from a human. Optionally, the framework region of the human antibody is aligned and adopted in accordance with the pertinent human germ line variable region sequences in the database; see, e.g., Vbase (vbase.mrc-cpe.cam.ac.uk) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody described herein is characterized by (i) being obtained using the human immune response rather than that of animal surrogates, i.e. the antibody has been generated in response to natural PNAd in its relevant conformation in the human body, (ii) having protected the individual or is at least significant for the presence of PNAd, and (iii) since the antibody is of human origin the risks of cross-reactivity against self-antigens is minimized. Thus, as used herein, the terms "human monoclonal antibody", "human monoclonal autoantibody", "human antibody" and the like are used to denote a PNAd binding molecule which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies described herein.

For example, the pairing of heavy and light chains of human-like antibodies such as synthetic and semi-synthetic antibodies typically isolated from phage display do not necessarily reflect the original pairing as it occurred in the original human B cell. Accordingly Fab and scFv fragments obtained from recombinant expression libraries as commonly used in the prior art can be considered as being artificial with all possible associated effects on immunogenicity and stability.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in a method described herein may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide described herein comprises a polypeptide chain comprising a CH3 domain. Further, a binding polypeptide for use in a method described herein may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers described herein are not identical. For example, each monomer may comprise a different target binding site, forming, for example, a bispecific antibody or diabody.

In some embodiments, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. In some embodiments, the light chain portion comprises at least one of a VL or CL domain.

The minimum size of a peptide or polypeptide epitope for an antibody is thought to be about four to five amino acids. Peptide or polypeptide epitopes may contain at least seven, at least nine or between at least about 15 to about 30 amino acids. Since a CDR can recognize an antigenic peptide or polypeptide in its tertiary form, the amino acids comprising an epitope need not be contiguous, and in some cases, may not even be on the same peptide chain. In some embodiments, a peptide or polypeptide epitope recognized by antibodies described herein contains a sequence of at least 4, at least 5, at least 6, at least 7, at least 8, at least 9, at least 10, at least 15, at least 20, at least 25, or between about 5 to about 30, about 10 to about 30 or about 15 to about 30 contiguous or non-contiguous amino acids of a PNAd.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. A skilled artisan understands that an antibody may specifically bind to, or specifically recognize an isolated polypeptide comprising, or consisting of, amino acid residues corresponding to a linear portion of a non-contiguous epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%. A skilled artisan understands that the binding of an antibody to its epitope may also be competitively inhibited by a binding molecule that is not an antibody.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, IC50, are preferably made with standardized solutions of antibody and antigen, and a standardized buffer.

Binding molecules, e.g., antibodies or antigen-binding fragments, variants or derivatives thereof described herein may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof described herein may also be described or specified in terms of their binding affinity to a PNAd.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083.

As used herein the term "disulfide bond" includes the covalent bond formed to between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product."

As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, plasma or urine. In other aspects, a sample can comprise whole blood, plasma, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 µl buffer (20 mM Tris, pH. 7.5, 0.5% Nonidet, 1 mM EDTA, 1 mM PMSF, 0.1M NaCl, IX Sigma Protease Inhibitor, and IX Sigma Phosphatase Inhibitors 1 and 2). The suspension can be kept on ice for 20 minutes with intermittent vortexing. After spinning at 15,000×g for 5 minutes at about 4° C., aliquots of supernatant can be stored at about −70° C.

As used herein, the terms "treat" or "treatment" refer to both therapeutic treatment and prophylactic or preventative measures, wherein the object is to prevent or slow down (lessen) an undesired physiological change or disorder described herein. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

By "subject" or "individual" or "animal" or "patient" or "mammal," is meant any subject, particularly a mammalian subject, e.g., a human patient, for whom diagnosis, prognosis, prevention, or therapy is desired.

A composition or method described herein that comprises components or steps can also consist essentially of, or consist of, those components or steps.

II. Antibodies

Provided are anti-peripheral lymph node addressin (PNAd) antibodies and antigen-binding fragments thereof. Also provided herein are derivatives or variants of the anti-PNAd antibodies or antigen-binding fragments thereof. Also provided herein are conjugates comprising such antibodies or PNAd-binding fragments thereof or derivatives or variants thereof. In some embodiments, an antibody or PNAd-binding fragment thereof described herein demonstrates the binding characteristics and/or biological properties as outlined for the antibody MHA112 illustrated in the Examples section below. As described in the Examples section below, anti-PNAd antibody MHA112 displays improved binding affinity to cells expressing PNAd (Example 6) and improved ability to block T cell homing to lymph nodes (Example 4). Administration of drug conjugated to MHA112 resulted in reduced tumor growth, reduced tumor metastasis, and reduced tumor-draining lymph node fibrosis (Example 7), in addition to increased survival time (Example 8). Moreover, administration of drug conjugated to MHA112 also increased survival time in pancreas tumor model (Example 9).

The antibodies and antigen-binding fragments thereof may be characterized by comprising in their variable region, e.g., binding domain, at least one complementarity determining region (CDR) of the VH and/or VL variable region comprising any one of the amino acid sequences depicted in FIG. 5. The corresponding nucleotide sequences encoding the above-identified variable regions are set forth in Table 4 below. An exemplary set of CDRs of the above amino acid sequences of the VH and/or VL region is depicted in FIG. 5 and Table 2. The corresponding framework regions for the CDRs of Table 2 are shown in Table 3. However, as discussed in the following the person skilled in the art is well aware of the fact that in addition or alternatively CDRs may be used, which differ in their amino acid sequence from those set forth in FIG. 5 by one, two, three or even more amino acids in case of CDR2 and CDR3.

TABLE 2

IMGT CDR Sequences.

| | CDR1 | CDR2 | CDR3 |
|---|---|---|---|
| Heavy Chain | GFSLTSY (SEQ ID NO: 3) | WGGGS (SEQ ID NO: 4) | HSKGGYFDV (SEQ ID NO: 5) |
| Light Chain | SASSSVSYMH (SEQ ID NO: 8) | EISKLAS (SEQ ID NO: 9) | QQWNYPLIT (SEQ ID NO: 10) |

TABLE 3

Framework Region Sequences

| | FR1 | FR2 | FR3 | FR4 |
|---|---|---|---|---|
| Heavy Chain | QVQLKESGPGL VAPSQSLSITCT VS (SEQ ID NO: 11) | GVDWVRQPPG KGLEWLGVI (SEQ ID NO: 12) | TNYNSALMSRL SISKDNSKSQVF LKMNSLQTDDT AMYYCAK (SEQ ID NO: 13) | WGTGTTVTVSS (SEQ ID NO: 14) |
| Light Chain | EIVLTQSPAITAA SLGQKVTITC (SEQ ID NO: 15) | WYQQKSGTSPK PWIY (SEQ ID NO: 16) | GVPARFSGSGS GTSYSLTISSME AEDAAIYYC (SEQ ID NO: 17) | FGAGTKLELK (SEQ ID NO: 18) |

TABLE 4

Variable Region Sequences

| | Nucleotide | Amino Acid |
|---|---|---|
| Heavy Chain | CAGGTGCAGCTGAAGGAGTCAGGACCTGG CCTGGTGGCGCCCTCACAGAGCCTGTCCAT CACTTGCACTGTCTCTGGGTTTTCATTAAC CAGCTATGGTGTAGACTGGGTTCGCCAGCC TCCAGGAAAGGGTCTGGAGTGGCTGGGAG TAATATGGGTGGTGGAAGCACAAATTAT AATTCAGCTCTCATGTCCAGACTGAGCATC AGCAAAGACAACTCCAAGAGCCAAGTTTT CTTAAAAATGAACAGTCTGCAAACTGATG ACACAGCCATGTACTACTGTGCCAAACAT AGTAAAGGGGGGTACTTCGATGTCTGGGG CACAGGGACCACGGTCACCGTCTCCTCA (SEQ ID NO: 1) | QVQLKESGPGL VAPSQSLSITCT VSGFSLTSYGV DWVRQPPGKGL EWLGVIWGGGS TNYNSALMSRL SISKDNSKSQVF LKMNSLQTDDT AMYYCAKHSK GGYFDVWGTG TTVTVSS (SEQ ID NO: 2) |
| Light Chain | GAAATTGTGCTCACTCAGTCTCCAGCCATC ACAGCTGCATCTCTGGGGCAAAAGGTCAC CATCACCTGCAGTGCCAGCTCAAGTGTAA GTTACATGCACTGGTACCAGCAGAAGTCA GGCACCTCCCCCAAACCATGGATTTATGAA ATATCCAAACTGGCTTCTGGAGTCCCAGCT CGCTTCAGTGGCAGTGGGTCTGGGACCTCT TACTCTCTCACAATCAGCAGCATGGAGGCT GAAGATGCTGCCATTTATTACTGCCAGCAG TGGAATTATCCTCTTATCACGTTCGGTGCT GGGACCAAGCTGGAGCTGAAA (SEQ ID NO: 6) | EIVLTQSPAITA ASLGQKVTITCS ASSSVSYMHWYQ QKSGTSPKPWIY EISKLASGVPAR FSGSGSGTSYSL TISSMEAEDAAI YYCQQWNYPLIT FGAGTKLELK (SEQ ID NO: 7) |

In some embodiments, an antibody or antigen-binding fragment thereof described herein comprises at least one CDR comprising, or consisting of an amino acid sequence selected from the group consisting of SEQ ID NOs: 3-5 and 8-10. In some embodiments, an antibody or antigen-binding fragment thereof described herein comprises one, two, three, four, five or six CDRs comprising, or consisting of an amino acid sequence selected from the group consisting of SEQ ID NO: 3-5 and 8-10 (see, e.g., Table 2).

In some embodiments, the antibody or antigen-binding fragment thereof comprises a heavy chain variable region (VH) complementarity determining region 1 (CDR1) comprising the amino acid sequence of SEQ ID NO:3, a VH CDR2 comprising the amino acid sequence of SEQ ID NO:4, and a VH CDR3 comprising the amino acid sequence of SEQ ID NO:5. In some embodiments, the antibody or PNAd-binding fragment thereof comprises a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5, and further comprises a light chain variable region (VL) CDR1 comprising the amino acid sequence of SEQ ID NO:8, a VL CDR2 comprising the amino acid sequence of SEQ ID NO:9, and a VL CDR3 comprising the amino acid sequence of SEQ ID NO:10.

In some embodiments, the antibody or PNAd-binding fragment thereof comprises a VL CDR1 comprising the amino acid sequence of SEQ ID NO:8, a VL CDR2 comprising the amino acid sequence of SEQ ID NO:9, and a VL CDR3 comprising the amino acid sequence of SEQ ID NO:10. In some embodiments, the antibody or PNAd-binding fragment thereof comprises a VL CDR1 comprising the amino acid sequence of SEQ ID NO:8, a VL CDR2 comprising the amino acid sequence of SEQ ID NO:9, and a VL CDR3 comprising the amino acid sequence of SEQ ID NO:10, and further comprises a VH CDR1 comprising the amino acid sequence of SEQ ID NO:3, a VH CDR2 comprising the amino acid sequence of SEQ ID NO:4, and a VH CDR3 comprising the amino acid sequence of SEQ ID NO:5.

In some embodiments, an antibody or antigen-binding fragment thereof described herein may comprise a VH comprising: (i) a VH CDR1 comprising the amino acid sequence of SEQ ID NO: 3; (ii) a VH CDR2 comprising the amino acid sequence of SEQ ID NO: 4; and (iii) a VH CDR3 comprising the amino acid sequence of SEQ ID NO: 5. In some embodiments, an antibody or antigen-binding fragment thereof described herein may comprise a light chain variable region (VL) comprising: (i) a VL CDR1 comprising the amino acid sequence of SEQ ID NO: 8; (ii) a VL CDR2 comprising the amino acid sequence of SEQ ID NO: 9; and (iii) a VL CDR3 comprising the amino acid sequence of SEQ ID NO: 10. In some embodiments, the antibody or PNAd-binding fragment thereof may further comprise a heavy chain variable region comprising a VH CDR1 of SEQ ID NO: 3; a VH CDR2 of SEQ ID NO: 4; and a VH CDR3 of SEQ ID NO: 5, and may further comprise a light chain variable region comprising a VL CDR1 of SEQ ID NO: 8; a VL CDR2 of SEQ ID NO: 9; and a VL CDR3 of SEQ ID NO: 10.

In some embodiments, an antibody or antigen-binding fragment thereof described herein may comprise a heavy chain variable region comprising a VH CDR1 comprising or consisting of SEQ ID NO: 3; a VH CDR2 comprising or consisting of SEQ ID NO: 4; and a VH CDR3 comprising or consisting of SEQ ID NO: 5.

In some embodiments, an antibody or antigen-binding fragment thereof described herein may comprise a light chain variable region comprising a VL CDR1 comprising or consisting of SEQ ID NO: 8; a VL CDR2 comprising or consisting of SEQ ID NO: 9; and a VL CDR3 comprising or consisting of SEQ ID NO: 10.

In some embodiments, an antibody or antigen-binding fragment thereof described herein may comprise a heavy chain variable region comprising a VH CDR1 comprising or consisting of SEQ ID NO: 3; a VH CDR2 comprising or consisting of SEQ ID NO: 4; and a VH CDR3 comprising or consisting of SEQ ID NO: 5, and may further comprise a light chain variable region comprising a VL CDR1 comprising or consisting of SEQ ID NO: 8; a VL CDR2 comprising or consisting of SEQ ID NO: 9; and a VL CDR3 comprising or consisting of SEQ ID NO: 10.

In some embodiments, an antibody or antigen-binding fragment thereof described herein comprises a VH comprising a heavy chain framework region 1 (FR1) comprising the amino acid sequence set forth in SEQ ID NO:11, a heavy chain FR2 comprising the amino acid sequence set forth in SEQ ID NO:12, a heavy chain FR3 comprising the amino acid sequence set forth in SEQ ID NO:13, and a heavy chain FR4 comprising the amino acid sequence set forth in SEQ ID NO:14.

In some embodiments, an antibody or antigen-binding fragment thereof described herein comprises a VL comprising a light chain FR1 comprising the amino acid sequence set forth in SEQ ID NO:15, a light chain FR2 comprising the amino acid sequence set forth in SEQ ID NO:16, a light chain FR3 comprising the amino acid sequence set forth in SEQ ID NO:17, and a light chain FR4 comprising the amino acid sequence set forth in SEQ ID NO:18.

In some embodiments, an antibody or antigen-binding fragment thereof described herein comprises a VH comprising a VH CDR1 comprising or consisting of SEQ ID NO: 3; a VH CDR2 comprising or consisting of SEQ ID NO: 4; and a VH CDR3 comprising or consisting of SEQ ID NO: 5, wherein the VH has at least 80%, at least 85%, at least 90%, at least 95%, at least 98%, or 100% sequence identity to the amino acid sequence of SEQ ID NO:2. In some embodiments, an antibody or antigen-binding fragment thereof described herein comprises a VH comprising a VH CDR1 comprising or consisting of SEQ ID NO: 3; a VH CDR2 comprising or consisting of SEQ ID NO: 4; and a VH CDR3 comprising or consisting of SEQ ID NO: 5, wherein the VH has 1 to 10 (e.g., 1, 2, 3, 4, 5, 6, 7, 8, 9, or 10) amino acid substitutions, additions, or deletions relative to the amino acid sequence of SEQ ID NO:2. In some instances, the amino acid substitutions are conservative amino acid substitutions.

In some embodiments, an antibody or antigen-binding fragment thereof described herein comprises a VL comprising VL CDR1 comprising or consisting of SEQ ID NO: 8; a VL CDR2 comprising or consisting of SEQ ID NO: 9; and a VL CDR3 comprising or consisting of SEQ ID NO: 10, wherein the VL has at least 80%, at least 85%, at least 90%, at least 95%, at least 98%, or 100% sequence identity to the amino acid sequence of SEQ ID NO:7. In some embodiments, an antibody or antigen-binding fragment thereof described herein comprises a VL comprising VL CDR1 comprising or consisting of SEQ ID NO: 8; a VL CDR2 comprising or consisting of SEQ ID NO: 9; and a VL CDR3 comprising or consisting of SEQ ID NO: 10, wherein the VL has 1 to 10 (e.g., 1, 2, 3, 4, 5, 6, 7, 8, 9, or 10) amino acid substitutions, additions, or deletions relative to the amino acid sequence of SEQ ID NO:7. In some instances, the amino acid substitutions are conservative amino acid substitutions.

In some embodiments, an antibody or antigen-binding fragment thereof described herein comprises: (a) a VH comprising a VH CDR1 comprising or consisting of SEQ ID NO: 3; a VH CDR2 comprising or consisting of SEQ ID NO: 4; and a VH CDR3 comprising or consisting of SEQ ID NO: 5, wherein the VH has at least 80%, at least 85%, at least 90%, at least 95%, at least 98%, or 100% sequence identity to the amino acid sequence of SEQ ID NO:2, and (b) a VL comprising VL CDR1 comprising or consisting of SEQ ID NO: 8; a VL CDR2 comprising or consisting of SEQ ID NO: 9; and a VL CDR3 comprising or consisting of SEQ ID NO: 10, wherein the VL has at least 80%, at least 85%, at least 90%, at least 95%, at least 98%, or 100% sequence identity to the amino acid sequence of SEQ ID NO:7. In some embodiments, an antibody or antigen-binding fragment thereof described herein comprises: (a) a VH comprising a VH CDR1 comprising or consisting of SEQ ID NO: 3; a VH CDR2 comprising or consisting of SEQ ID NO: 4; and a VH CDR3 comprising or consisting of SEQ ID NO: 5, wherein the VH has 1 to 10 (e.g., 1, 2, 3, 4, 5, 6, 7, 8, 9, or 10) amino acid substitutions, additions, or deletions relative to the amino acid sequence of SEQ ID NO:2; and (b) a VL comprising VL CDR1 comprising or consisting of SEQ ID NO: 8; a VL CDR2 comprising or consisting of SEQ ID NO: 9; and a VL CDR3 comprising or consisting of SEQ ID NO: 10, wherein the VL has 1 to 10 (e.g., 1, 2, 3, 4, 5, 6, 7, 8, 9, or 10) amino acid substitutions, additions, or deletions relative to the amino acid sequence of SEQ ID NO:7. In some embodiments, the substitutions are conservative substitutions. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, a variant of an antibody described herein (e.g., an antibody or antigen-binding fragment thereof having amino acid substitutions, additions, or deletions relative to the VH and/or VL of the amino acid sequences set forth in SEQ ID NOs: 2 and 7, respectively) retains the ability to bind PNAd and/or retains one or more characteristics of the antibody MHA112 described in the examples below.

In some embodiments, an antibody or antigen-binding fragment thereof described herein comprises a heavy chain variable region (VH) comprising, or consisting of the amino acid sequence of SEQ ID NO: 2. In some embodiments, an antibody or antigen-binding fragment thereof described herein comprises a light chain variable region (VL) comprising, or consisting of the amino acid sequence of SEQ ID NO: 7. In some embodiments, an antibody or antigen-binding fragment thereof described herein comprises a heavy chain variable region (VH) comprising, or consisting of the amino acid sequence of SEQ ID NO: 2, and further comprises a light chain variable region (VL) comprising, or consisting of the amino acid sequence of SEQ ID NO: 7. In some embodiments, the antibody or antigen-binding fragment thereof comprises a VH of SEQ ID NO: 2 and a VL of SEQ ID NO: 7.

In some embodiments, an antibody described herein comprises a heavy chain comprising a VH described herein. In some instances, the heavy chain comprises an IgM constant region. In some instances, the heavy chain comprises a human IgM constant region.

In some embodiments, an antibody described herein comprises a light chain comprising a VL described herein. In some instances, the light chain comprises a kappa constant region. In some instances, the light chain comprises a human kappa constant region. In some instances, the light chain comprises a lambda constant region. In some instances, the light chain comprises a human lambda constant region.

In some embodiments, an antibody thereof described herein comprises a heavy chain comprising a VH described herein and a light chain comprising a VL described herein, wherein the heavy chain comprises an IgM (e.g., a human IgM) constant region and the light chain comprises a kappa (e.g., a human kappa) constant region. In some embodiments, an antibody described herein comprises a heavy chain comprising a VH described herein and a light chain comprising a VL described herein, wherein the heavy chain comprises an IgM (e.g., a human IgM) constant region and the light chain comprises a lambda (e.g., a lambda kappa) constant region.

Alternatively, the antibody described herein is an antibody or antigen-binding fragment, derivative or variant thereof, which competes for binding to PNAd with an antibody having VH CDRs 1-3 set forth in SEQ ID NOs:3-5, respectively. Alternatively, the antibody described herein is an antibody or antigen-binding fragment, derivative, or variant thereof, which competes for binding to PNAd with an antibody having the VL CDRs 1-3 set forth in SEQ ID NOs: 8-10. Alternatively, the antibody described herein is an antibody or antigen-binding fragment, derivative, or variant thereof, which competes for binding to PNAd with an antibody having VH CDRs 1-3 set forth in SEQ ID Nos: 3-5, respectively, and VL CDRs 1-3 set forth in SEQ ID NOs: 8-10, respectively. Alternatively, the antibody described herein is an antibody or antigen-binding fragment, derivative, or variant thereof, which competes for binding to PNAd with an antibody having the VH and/or VL set forth in SEQ ID NOs: 2 and 7, respectively. Those antibodies may be human, rodent (e.g., murine), chimeric, or humanized, in particular for therapeutic applications.

Alternatively, the antibody described herein is an antibody or antigen-binding fragment, derivative or variant thereof, which binds to the same epitope as an anti-PNAd antibody comprising a VH of SEQ ID NO:2 and a VL of SEQ ID NO:7.

Competition between antibodies is determined by an assay in which the immunoglobulin under test inhibits specific binding of a reference antibody to a common antigen, such as PNAd. Numerous types of competitive binding assays are known, for example: solid phase direct or indirect radioimmunoassay (RIA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using 1125 label; see Morel et al, Molec. Immunol. 25 (1988), 7-15 and Moldenhauer et al., Scand. J. Immunol. 32 (1990), 77-82. Typically, such an assay involves the use of purified PNAd or aggregates thereof bound to a solid surface or cells bearing either of these, an unlabeled test immunoglobulin and a labeled reference immunoglobulin, i.e. the human monoclonal antibody described herein. Competitive inhibition is measured by determining the amount of label bound to the solid surface or cells in the presence of the test immunoglobulin. Usually the test immunoglobulin is present in excess. In some embodiments, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody comprising a VH of SEQ ID NO:2 and a VL of SEQ ID NO:7 from binding to PNAd.

In some embodiments, provided herein are isolated polypeptides comprising an immunoglobulin heavy chain variable region (VH), where at least one of the VH-CDRs of the heavy chain variable region or at least two of the VH-CDRs of the heavy chain variable region are at least 80%, 85%, 90%, 95%, 96%, 97%, 98% or 99% identical to reference heavy chain VH-CDR1, VH-CDR2 or VH-CDR3 amino acid sequences from an antibody disclosed herein (see, e.g., Table 2 for VH CDR sequences). Alternatively, the VH-CDR1, VH-CDR2 and VH-CDR3 regions of the VH are at least 80%, 85%, 90%, 95%, 96%, 97%, 98% or 99% identical to reference heavy chain VH-CDR1, VH-CDR2 and VH-CDR3 amino acid sequences from an antibody disclosed herein (see, e.g., Table 2 for VH CDR sequences). Thus, a heavy chain variable region described herein can have VH-CDR1, VH-CDR2 and VH-CDR3 polypeptide sequences related to sequences of Table 2 (i.e., SEQ ID NOs:3-5). While Table 2 shows VH-CDRs defined by the IMGT system, other CDR definitions, e.g., VH-CDRs defined by the Kabat or Chothia system, are also included in the present invention, and can be easily identified by a person of ordinary skill in the art using the sequences presented in Tables 2-4. In some embodiments, the amino acid sequence of the reference VH CDR1 is SEQ ID NO:3; the amino acid sequence of the reference VH CDR2 is SEQ ID NO: 4; and the amino acid sequence of the reference VH CDR3 is SEQ ID NO: 5.

The isolated polypeptides described herein can comprise an immunoglobulin heavy chain variable region (VH) in which the VH-CDR1, VH-CDR2 and VH-CDR3 regions have polypeptide sequences that are identical to the VH-CDR1, VH-CDR2 and VH-CDR3 sequences shown in Table 2 (i.e., SEQ ID NOs:3-5). In some embodiments, the amino acid sequence of the VH CDR1 is SEQ ID NO: 3; the amino acid sequence of the VH CDR2 is SEQ ID NO: 4; and the amino acid sequence of the VH CDR3 is SEQ ID NO: 5.

Further, the isolated polypeptides can comprise an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 sequences shown in Table 2, except for one, two, three, four, five, six, seven, eight, nine, or ten amino acid substitutions in any one VH-CDR. In some embodiments, the amino acid substitutions are conservative. In some embodiments, the amino acid sequence of the VH CDR1 is SEQ ID NO: 3; the amino acid sequence of the VH CDR2 is SEQ ID NO: 4; and the amino acid sequence of the VH CDR3 is SEQ ID NO: 5.

The isolated polypeptides can comprise an immunoglobulin light chain variable region (VL), where at least one of the VL-CDRs of the light chain variable region or at least two of the VL-CDRs of the light chain variable region are at least 80%, 85%, 90%, 95%, 96%, 97%, 98% or 99% identical to reference light chain VL-CDR1, VL-CDR2 or VL-CDR3 amino acid sequences from an antibody disclosed herein (see, e.g., Table 2 for VL CDR sequences). Alternatively, the VL-CDR1, VL-CDR2 and VL-CDR3 regions of the VL can be at least 80%, 85%, 90%, 95%, 96%, 97%, 98% or 99% identical to reference light chain VL-CDR1, VL-CDR2 and VL-CDR3 amino acid sequences from an antibody disclosed herein (see e.g., Table 2 for VL CDR sequences). Thus, the light chain variable region can have VL-CDR1, VL-CDR2 and VL-CDR3 polypeptide sequences related to the sequences of Table 2 (i.e., SEQ ID NOs: 8-10). While Table 2 shows VL-CDRs defined by the IMGT system, other CDR definitions, e.g., VL-CDRs defined by the Kabat or Chothia system, are also included in the present invention. In some embodiments, the amino acid sequence of the reference VL CDR1 is SEQ ID NO:8; the amino acid sequence of the reference VL CDR2 is SEQ ID NO:9; and the amino acid sequence of the reference VL CDR3 is SEQ ID NO:10.

Also provided herein are isolated polypeptides comprising an immunoglobulin light chain variable region (VL) in which the VL-CDR1, VL-CDR2 and VL-CDR3 regions have polypeptide sequences that are identical to the VL-CDR1, VL-CDR2 and VL-CDR3 sequences of Table 2. In some embodiments, the amino acid sequence of the VL CDR1 is SEQ ID NO:8; the amino acid sequence of the VL CDR2 is SEQ ID NO:9; and the amino acid sequence of the VL CDR3 is SEQ ID NO:10.

The isolated polypeptides can also comprise an immunoglobulin light chain variable region (VL) in which the VL-CDR1, VL-CDR2 and VL-CDR3 regions have polypeptide sequences that are identical to the VL-CDR1, VL-CDR2 and VL-CDR3 sequences of Table 2, except for one, two, three, four, five, six, seven, eight, nine, or ten amino acid substitutions in any one VL-CDR. In some embodiments, the amino acid substitutions are conservative. In some embodiments, the amino acid sequence of the VL CDR1 is SEQ ID NO:8; the amino acid sequence of the VL CDR2 is SEQ ID NO:9; and the amino acid sequence of the VL CDR3 is SEQ ID NO:10.

An immunoglobulin or its encoding cDNA can be modified. Thus, the methods described herein can include any one of the step(s) of producing a chimeric antibody, humanized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies that bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody described herein may exist in a variety of forms besides complete antibodies; including, for example, Fv, Fab and F(ab)2, as well as in single chains; see e.g. international application WO88/09344. Antibodies made by such methods are also provided herein.

The antibodies described herein or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody described herein include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins, which comprise the described antibody or some fragment thereof at the amino terminus fused to heterologous molecule such as an immunostimulatory ligand at the carboxyl terminus; see, e.g., international application WO00/30680 for corresponding technical details.

Additionally, provided herein are peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent as described herein. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, described herein are binding molecules, e.g., an antibody or binding fragment thereof that is bind the human anti-PNAd antibodies described herein and display the mentioned properties, i.e., that specifically recognize (bind to) PNAd. Such antibodies and binding molecules can be tested for their binding specificity and affinity by ELISA and Western Blot and immunohistochemistry as described herein, see, e.g., the Examples.

As an alternative to obtaining immunoglobulins directly from the culture of immortalized B cells or B memory cells, the immortalized cells described herein can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells may be considered. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are designed to include signal peptides so that the resulting antibodies are secreted into the medium; however, intracellular production is also possible.

In accordance with the above, the present invention also relates to a polynucleotide encoding the antibody or equivalent binding molecule described herein. In some embodiments, the polynucleotide encodes at least a variable region of an immunoglobulin chain of the antibody described above. Typically, said variable region encoded by the polynucleotide comprises at least one complementarity determining region (CDR) of the VH and/or VL of the variable region of the said antibody.

A person skilled in the art will readily appreciate that the variable domain of an antibody having an above-described variable domains can be used for the construction of other polypeptides or antibodies of desired specificity and biological function. Thus, provided herein are polypeptides and antibodies comprising at least one or more CDR, e.g., all of the CDRs, of the above-described variable domains and that advantageously have substantially the same or similar binding properties as the antibody described in the appended examples. The person skilled in the art knows that binding affinity can be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, antibodies wherein one or more of the mentioned CDRs comprise one or more, or not more than two amino acid substitutions, also provided herein. In some embodiments, the antibody described herein comprises in one or both of its immunoglobulin chains two or all three CDRs of the variable regions as set forth in Table 2.

Binding molecules, e.g., antibodies, or antigen-binding fragments, variants, or derivatives thereof described herein, as known by those of ordinary skill in the art, can comprise a constant region, which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, some embodiments described herein include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of PNAd, reduced serum half-life, or increased serum half-life when compared with a whole, unaltered antibody of approximately the same immunogenicity. For example, some antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgM heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO2005/018572, which is incorporated by reference in its entirety.

In certain antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing PNAd localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as PNAd localization, biodistribution and serum half-life, may easily be measured and quantified using well know immunological techniques without undue experimentation.

In some antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody-binding region and the cognate protein ligands of cell surface receptors or bi- or multi-specific antibodies with a specific sequences biding to PNAd as well as a cell surface receptor may be engineered using techniques known in the art.

In some antibodies, or antigen-binding fragments, variants, or derivatives thereof described herein, the Fc portion may be mutated or exchanged for alternative protein sequences or the antibody may be chemically modified to increase its blood brain barrier penetration.

Modified forms of antibodies, or antigen-binding fragments, variants, or derivatives thereof described herein can be made from whole precursor or parent antibodies using techniques known in the art. Exemplary techniques are discussed in more detail herein. Antibodies, or antigen-binding fragments, variants, or derivatives thereof described herein can be made or manufactured using techniques that are known in the art. In some embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof described herein also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In some embodiments, antibodies, or antigen-binding fragments, variants, or derivatives thereof described herein will not elicit a deleterious immune response in the animal to be treated, e.g., in a human. In some embodiments, binding molecules, e.g., antibodies, or antigen-binding fragments thereof described herein are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, VH and VL sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., PNAd-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology.

In a well-known hybridoma process (Kohler et al., Nature 256 (1975), 495) the relatively short-lived, or mortal, lymphocytes from a mammal, e.g., B cells derived from a murine subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that contain one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press, pp 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In some embodiments, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific immunoglobulins that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the methods and compositions as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and F(ab')2 fragments may be produced recombinantly or by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

In some embodiments, an antibody described herein comprises at least one heavy or light chain CDR of an antibody molecule. In another embodiment, an antibody described herein comprises at least two CDRs from one or more antibody molecules. In another embodiment, an antibody described herein comprises at least three CDRs from one or more antibody molecules. In another embodiment, an antibody described herein comprises at least four CDRs from one or more antibody molecules. In another embodiment, an antibody described herein comprises at least five CDRs from one or more antibody molecules. In another embodiment, an antibody described herein comprises at least six CDRs from one or more antibody molecules. Exemplary antibody molecules comprising at least one CDR that can be included in the subject antibodies are described herein.

Antibodies described herein can be produced by any method known in the art for the synthesis of antibodies, in particular, by chemical synthesis or by recombinant expression techniques as described herein.

In some embodiments, an antibody, or antigen-binding fragment, variant, or derivative thereof described herein comprises a synthetic constant region wherein one or more domains are partially or entirely deleted ("domain-deleted antibodies"). In some embodiments compatible modified antibodies will comprise domain deleted constructs or variants wherein the entire CH2 domain has been removed. For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG1 human constant domain, see, e.g., international applications WO02/060955 and WO02/096948A2. This vector is engineered to delete the CH2 domain and provide a synthetic vector expressing a domain deleted IgG1 constant region.

In some embodiments, antibodies, or antigen-binding fragments, variants, or derivatives thereof described herein are minibodies. Minibodies can be made using methods described in the art, see, e.g., U.S. Pat. No. 5,837,821 or international application WO 94/09817.

In some embodiments, an antibody, or antigen-binding fragment, variant, or derivative thereof described herein comprises an immunoglobulin heavy chain having deletion or substitution of a few or even a single amino acid as long as it permits association between the monomeric subunits and retains binding to PNAd. For example, the mutation of a single amino acid in selected areas of the CH2 domain may be enough to substantially reduce Fc binding and thereby increase PNAd localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments, it may be desirable to insert or replicate specific sequences derived from selected constant region domains.

The present invention also provides antibodies that comprise, consist essentially of, or consist of, variants (including derivatives) of antibody molecules (e.g., the VH regions and/or VL regions) described herein, which antibodies or fragments thereof immunospecifically bind to PNAd. Standard techniques known to those of skill in the art can be used to introduce mutations in the nucleotide sequence encoding an antibody, including, but not limited to, site-directed mutagenesis and PCR-mediated mutagenesis which result in amino acid substitutions. In some embodiments, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VH-CDR1, VH-CDR2, VH-CDR3, VL region, VL-CDR1, VL-CDR2, or VL-CDR3. Alternatively, mutations can be introduced randomly along all or part of the coding sequence, such as by saturation mutagenesis, and the resultant mutants can be screened for biological activity to identify mutants that retain activity (e.g., the ability to bind PNAd).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies described herein are disclosed elsewhere herein. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of PNAd) can be determined using techniques described herein or by routinely modifying techniques known in the art.

PNAd-binding agents, for example, but not limited to, PNAd-binding antibodies described herein may be characterized using any in vivo or in vitro models. A skilled artisan readily understands that a PNAd binding agent (e.g., an antibody) described herein may be characterized in a mouse model described herein.

III. Polynucleotides Encoding Antibodies

Also provided herein are polynucleotides encoding an antibody, or antigen-binding fragment, variant, or derivative thereof described herein. A polynucleotide encoding an antibody, or antigen-binding fragment, variant, or derivative thereof can be composed of any polyribonucleotide or polydeoxyribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. In some embodiments, conservative amino acid substitutions are made at one or more non-essential amino acid residues.

As is well known, RNA may be isolated from the original B cells, hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In some embodiments, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In some embodiments, provided herein is an isolated polynucleotide comprising, consisting essentially of, or consisting of a nucleic acid encoding an immunoglobulin heavy chain variable region (VH), where at least one of the CDRs of the heavy chain variable region or at least two of the VH-CDRs of the heavy chain variable region are at least 80%, 85%, 90%, 95%, 96%, 97%, 98%, or 99% identical to reference heavy chain VH-CDR1, VH-CDR2, or VH-CDR3 amino acid sequences from the antibodies disclosed herein. Alternatively, the VH-CDR1, VH-CDR2, or VH-CDR3 regions of the VH are at least 80%, 85%, 90%, 95%, 96%, 97%, 98%, or 99% identical to reference heavy chain VH-CDR1, VH-CDR2, and VH-CDR3 amino acid sequences from the antibodies disclosed herein. Thus, according to this embodiment a heavy chain variable region of an antibody or antigen-binding fragment thereof described herein has VH-CDR1, VH-CDR2, or VH-CDR3 polypeptide sequences related to the polypeptide sequences shown in FIG. 5. In some embodiments, the amino acid sequence of the reference VH CDR1 is SEQ ID NO: 3; the amino acid sequence of the reference VH CDR2 is SEQ ID NO: 4; and the amino acid sequence of the reference VH CDR3 is SEQ ID NO: 5.

In some embodiments, provided herein is an isolated polynucleotide comprising, consisting essentially of, or consisting of a nucleic acid encoding an immunoglobulin heavy chain variable region (VH), in which the VH-CDR1, VH-CDR2 and VH-CDR3 regions have polypeptide sequences which are identical to the VH-CDR1, VH-CDR2 and VH-CDR3 groups shown in FIG. 5, except for one, two, three, four, five, six, seven, eight, nine, or ten amino acid substitutions in any one VH-CDR. In some embodiments, the amino acid substitutions are conservative. In some embodiments, the amino acid sequence of the VH CDR1 is SEQ ID NO: 3; the amino acid sequence of the VH CDR2 is SEQ ID NO: 4; and the amino acid sequence of the VH CDR3 is SEQ ID NO: 5.

In another embodiment, provided herein is an isolated polynucleotide comprising, consisting essentially of, or consisting of a nucleic acid encoding an immunoglobulin light chain variable region (VL), where at least one of the VL-CDRs of the light chain variable region or at least two of the VL-CDRs of the light chain variable region are at least 80%, 85%, 90%, 95%, 96%, 97%, 98%, or 99% identical to reference light chain VL-CDR1, VL-CDR2, or VL-CDR3 amino acid sequences from the antibodies disclosed herein. Alternatively, the VL-CDR1, VL-CDR2, or VL-CDR3 regions of the VL are at least 80%, 85%, 90%, 95%, 96%, 97%, 98%, or 99% identical to reference light chain VL-CDR1, VL-CDR2, and VL-CDR3 amino acid sequences from the antibodies disclosed herein. Thus, according to this embodiment a light chain variable region of the antibody or antigen-binding fragment thereof described herein has VL-CDR1, VL-CDR2, or VL-CDR3 polypeptide sequences related to the polypeptide sequences shown in FIG. 5. In some embodiments, the amino acid sequence of the reference VL CDR1 is SEQ ID NO: 8; the amino acid sequence of the reference VL CDR2 is SEQ ID NO: 9; and the amino acid sequence of the reference VL CDR3 is SEQ ID NO: 10.

In another embodiment, provided herein is an isolated polynucleotide comprising, consisting essentially of, or consisting of a nucleic acid encoding an immunoglobulin light chain variable region (VL) in which the VL-CDR1, VL-CDR2 and VL-CDR3 regions have polypeptide sequences which are identical to the VL-CDR1, VL-CDR2 and VL-CDR3 groups shown in FIG. 5, except for one, two, three, four, five, six, seven, eight, nine, or ten amino acid substitutions in any one VL-CDR. In some embodiments the amino acid substitutions are conservative. In some embodiments, the amino acid sequence of the VL CDR1 is SEQ ID NO: 8; the amino acid sequence of the VL CDR2 is SEQ ID NO: 9; and the amino acid sequence of the VL CDR3 is SEQ ID NO: 10.

In another embodiment, provided herein is an isolated polynucleotide comprising, consisting essentially of, or consisting of a nucleic acid encoding an immunoglobulin heavy chain variable region (VH) in which the VH-CDR1, VH-CDR2, and VH-CDR3 regions have polypeptide sequences that are identical to the VH-CDR1, VH-CDR2, and VH-CDR3 groups shown in FIG. 5. In some embodiments, the amino acid sequence of the VH CDR1 comprises SEQ ID NO: 3; the amino acid sequence of the VH CDR2 comprises SEQ ID NO: 4; and the amino acid sequence of the VH CDR3 comprises SEQ ID NO: 5. In some embodiments, the amino acid sequence of the VH CDR1 consists of SEQ ID NO: 3; the amino acid sequence of the VH CDR2 consists of SEQ ID NO: 4, and the amino acid sequence of the VH CDR3 consists of SEQ ID NO: 5.

In another embodiment, provided herein is an isolated polynucleotide comprising, consisting essentially of, or consisting of a nucleic acid encoding an immunoglobulin light chain variable region (VL) in which the VL-CDR1, VL-CDR2, and VL-CDR3 regions have polypeptide sequences which are identical to the VL-CDR1, VL-CDR2, and VL-CDR3 groups shown in FIG. 5. In some embodiments, the amino acid sequence of the VL CDR1 is SEQ ID NO: 8; the amino acid sequence of the VL CDR2 is SEQ ID NO: 9; and the amino acid sequence of the VL CDR3 is SEQ ID NO: 10. In some embodiments, the amino acid sequence of the VL CDR1 consists of SEQ ID NO: 8; the amino acid sequence of the VL CDR2 consists of SEQ ID NO: 9, and the amino acid sequence of the VL CDR3 consists of SEQ ID NO: 10.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence described herein (e.g., an antibody or antigen-binding fragment thereof described herein), the parameters are set, of course, such that the percentage of identity is calculated over the full length of the reference polypeptide sequence and that gaps in homology of up to 5% of the total number of amino acids in the reference sequence are allowed.

In some embodiments, the polynucleotide comprises, consists essentially of, or consists of a nucleic acid having a polynucleotide sequence of the VH or VL region of an anti-PNAd antibody as depicted in Table 4. In this respect, the person skilled in the art will readily appreciate that the polynucleotides encoding at least the variable domain of the light and/or heavy chain may encode the variable domain of both immunoglobulin chains or only one. Further provided herein is a polynucleotide comprising, or consisting of a nucleotide sequence encoding the amino acid sequence of SEQ ID: 2 (e.g., the nucleotide sequence of SEQ ID NO:1) and/or SEQ ID NO: 7 (e.g., the nucleotide sequence of SEQ ID NO: 6). In a specific embodiment, provided herein is a polynucleotide comprising, or consisting of a nucleotide sequence encoding the amino acid sequence of SEQ ID: 2 (e.g., the nucleotide sequence of SEQ ID NO:1). In another specific embodiment, provided herein is a polynucleotide comprising, or consisting of a nucleotide sequence encoding the amino acid sequence of SEQ ID: 7 (e.g., the nucleotide sequence of SEQ ID NO:6).

In some embodiments, provided herein is an isolated polynucleotide comprising, consisting essentially of, or consisting of a nucleic acid encoding an immunoglobulin heavy chain variable region at least 80%, 85%, 90%, 95%, 96%, 97%, 98%, or 99% or 95% identical to reference heavy chain VH. In some embodiments, the amino acid sequence of the reference heavy chain variable region is SEQ ID NO: 2.

In some embodiments, provided herein is an isolated polynucleotide comprising, consisting essentially of, or consisting of a nucleic acid encoding an immunoglobulin light chain variable region at least 80%, 85%, 90%, 95%, 96%, 97%, 98%, or 99% or 95% identical to reference light chain VL. In some embodiments, the amino acid sequence of the reference light chain variable region is SEQ ID NO: 7.

Also provided herein are fragments of the polynucleotides described herein, as described elsewhere. Additionally polynucleotides which encode fusion polynucleotides, Fab fragments, and other derivatives, as described herein, are also contemplated.

The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA+ RNA, isolated from, any tissue or cells expressing the PNAd-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof described herein, the polynucleotides encoding the antibodies are typically inserted in an expression vector for introduction into host cells that may be used to produce the desired quantity of antibody. Recombinant expression of an antibody, or fragment, derivative or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), described herein has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Thus, provided herein are replicable vectors comprising a nucleotide sequence encoding an antibody molecule, or antigen-binding fragment thereof, described herein, or a heavy or light chain thereof, or a heavy or light chain variable domain, operably linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance methods described herein as a vehicle for introducing into and expressing a desired gene in a host cell. As known to those skilled in the art, such vectors may easily be selected from the group consisting of plasmids, phages, viruses and retroviruses. In general, vectors described herein will comprise a selection marker, appropriate restriction sites to facilitate cloning of the desired gene and the ability to enter and/or replicate in eukaryotic or prokaryotic cells. Numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particular embodiments, the cloned variable region genes are inserted into an expression vector along with the heavy and light chain constant region genes (e.g., human heavy and light chain constant region genes) as discussed above. Any expression vector which is capable of eliciting expression in eukaryotic cells may be used. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the antibodies, or antigen-binding fragments, variants, or derivatives thereof described herein may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, also provided herein are host cells containing a polynucleotide encoding an antibody or antigen binding fragment thereof described herein, or a heavy or light chain thereof, operably linked to a heterologous promoter. In particular embodiments, for the expression of double-chained antibodies, vectors encoding both the heavy and light chains may be co-expressed in the host cell for expression of the entire immunoglobulin molecule, as detailed below.

The host cell may be co-transfected with two expression vectors described herein, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule described herein in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some embodiments, bacterial cells such as *Escherichia coli*, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). In a specific embodiment, host cell lines are CHO or 293 cells. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad.

Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981), which are incorporated by reference herein in their entireties.

The expression levels of an antibody molecule can be increased by vector amplification, for a review, see Bebbington and Hentschel, The use of vectors based on gene amplification for the expression of cloned genes in mammalian cells in DNA cloning, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding antibodies, or antigen-binding fragments, variants, or derivatives thereof described herein can also be expressed in non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody described herein has been recombinantly expressed, the whole antibodies, their dimers, individual light and heavy chains, or other immunoglobulin forms described herein, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Alternatively, another method for increasing the affinity of antibodies described herein is disclosed in US patent publication 2002-0123057 A1.

V. Fusion Proteins and Conjugates

In some embodiments, the antibody polypeptide comprises an amino acid sequence or one or more moieties not normally associated with an antibody. Exemplary modifications are described in more detail below. For example, a single-chain fv antibody fragment described herein may comprise a flexible linker sequence, or may be modified to add a functional moiety (e.g., PEG, a drug, a toxin, or a label such as a fluorescent, radioactive, enzyme, nuclear magnetic, heavy metal and the like)

An antibody polypeptide described herein may comprise, consist essentially of, or consist of a fusion protein. Fusion proteins are chimeric molecules which comprise, for example, an immunoglobulin PNAd-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof described herein may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

In some instances, the antibody or antigen-binding fragment thereof is conjugated to a drug. Methods of producing such drug conjugates are known in the art and described herein (see, e.g., Examples 7-9, below). In some instances, the drug is an immunosuppressive drug (see, e.g., the section "Immunosuppressive or Immunoregulatory Drugs" below for examples of immunosuppressive drugs. In some instances, the drug is taxol. In some instances, the drug directly is conjugated to the antibody or antigen-binding fragment thereof. In some instances, the drug is conjugated to the antibody or antigen-binding fragment thereof via a linker. Examples of linkers that may be used to conjugate a drug to an antibody or antigen-binding fragment thereof described herein include succinimidyl 4-(N-maleimidomethyl)cyclohexane-1-carboxylate (SMCC) or maleimidocaproyl-valine-citrulline-p-aminobenzoyloxycarbonyl (mc-vc-PAB). In some instances, the drug is covalently conjugated to the antibody or antigen-binding fragment thereof. Covalent conjugation of the drug to the antibody or antigen-binding fragment thereof may be performed as described in the Examples section below. For example, the drug may be chemically modified using, e.g., glutaraldehyde, to produce a carboxylic acid group, which is then activated using 1-ethyl-3-(3-dimethylaminopropyl)carbodiimide hydrochloride (EDC)/N-hydroxysulfosuccinimide (NHS) chemistry; the resulting drug preferentially reacts with (i.e., conjugates to) primary amines on the antibody or antigen-binding fragment thereof (e.g., such as those on lysines).

Antibodies, or antigen-binding fragments, variants, or derivatives thereof described herein can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., Proteins—Structure And Molecular Properties, T. E. Creighton, W. H. Freeman and Company, New York 2nd Ed., (1993); Posttranslational Covalent Modification Of Proteins, B. C. Johnson, Ed., Academic Press, New York, pgs. 1-12 (1983); Seifter et al., Meth. Enzymol. 182 (1990), 626-646; Rattan et al., Ann. NY Acad. Sci. 663 (1992), 48-62).

Also provided herein are fusion proteins comprising an antibody, or antigen-binding fragment, variant, or derivative thereof, and a heterologous polypeptide. In some embodiments, a fusion protein comprises, consists essentially of, or consists of, a polypeptide having the amino acid sequence of any one or more of the VH regions of an antibody described herein or the amino acid sequence of any one or more of the VL regions of an antibody described herein or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the VH-CDRs of an antibody, or fragments, variants, or derivatives thereof, or the amino acid sequence of any one, two, three of the VL-CDRs of an antibody, or fragments, variants, or derivatives thereof, and a heterologous polypeptide sequence. In some embodiments, the fusion protein comprises a polypeptide having the amino acid sequence of a VH-CDR3 of an antibody described herein, or fragment, derivative, or variant thereof, and a heterologous polypeptide sequence, which fusion protein specifically binds to PNAd. In another embodiment, a fusion protein comprises a polypeptide having the amino acid sequence of at least one VH region of an antibody described herein and the amino acid sequence of at least one VL region of an antibody described herein or fragments, derivatives or variants thereof, and a heterologous polypeptide sequence. In some embodiments, the VH and VL regions of the fusion protein correspond to a single source antibody (or scFv or Fab fragment) which specifically binds PNAd. In yet another embodiment, a fusion protein for use in the diagnostic and treatment methods disclosed herein comprises a polypeptide having the amino acid sequence of any one, two, three or more of the VH CDRs of an antibody and the amino acid sequence of any one, two, three or more of the VL CDRs of an antibody, or fragments or variants thereof, and a heterologous polypeptide sequence. In some embodiments, two, three, four, five, six, or more of the VH-CDR(s) or VL-CDR(s) correspond to single source antibody (or scFv or Fab fragment) described herein. Nucleic acid molecules encoding these fusion proteins are also provided herein.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof described herein may be fused to heterologous polypeptides to increase the in vivo half-life of the polypeptides or for use in immunoassays using methods known in the art. For example, In some embodiments, PEG can be conjugated to the antibodies described herein to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof described herein can be fused to marker sequences, such as a peptide to facilitate their purification or detection. In particular embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767) and the "flag" tag.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression.

Antibodies described herein may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof described herein can be labeled or conjugated either before or after purification, when purification is performed. In particular, antibodies, or antigen-binding fragments, variants, or derivatives thereof described herein may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies described herein can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared e.g. by reacting a PNAd binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, or fluorescein-isothiocyanate. Conjugates of the antibodies, or antigen-binding fragments, variants or derivatives thereof described herein are prepared in an analogous manner.

Also provided herein are antibodies, or antigen-binding fragments, variants, or derivatives thereof described herein conjugated to a diagnostic or therapeutic agent. The antibodies can be used diagnostically to, for example, demonstrate presence of a PNAd-related disease, to indicate the risk of getting a PNAd-related disease, to monitor the development or progression of a PNAd-related disease, i.e. as part of a clinical testing procedure to, e.g., determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), Enzyme Immunoassay, CRC Press, Boca Raton, Fla., (1980); Ishikawa, E. et al., (eds.), Enzyme Immunoassay, Kgaku Shoin, Tokyo (1981). The enzyme, which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, In some embodiments, a moiety that enhances the stability or efficacy of a binding molecule, e.g., a binding polypeptide, e.g., an antibody or immunospecific fragment thereof can be conjugated. For example, In some embodiments, PEG can be conjugated to the binding molecules described herein to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

A. Drug-Containing Polymeric Particles

Also provided herein are nano- or microparticles conjugated to an antibody or antigen-binding fragment thereof described herein. The nano- or microparticles described herein can be made of materials that (i) are biocompatible, i.e., do not cause a significant adverse reaction in a living animal when used in pharmaceutically relevant amounts; (ii) feature functional groups to which a lymphocyte homing adhesion molecule or an antibody or antigen-binding fragment thereof described herein can be covalently attached, (iii) exhibit low non-specific binding to other molecules, and (iv) are stable in solution, i.e., the particles do not precipitate. The particles can be monodisperse (a single crystal of a material, e.g., a metal, per particle) or polydisperse (a plurality of crystals, e.g., 2, 3, or 4, per particle).

A number of biocompatible particles are known in the art, e.g., organic or inorganic nano- or microparticles. Liposomes, dendrimers, carbon materials and polymeric micelles are examples of organic particles. Quantum dots can also be used. Inorganic particles include metallic particle, e.g., Au, Ni, Pt and TiO2 nano- or microparticles. Magnetic particles can also be used, e.g., spherical nanocrystals of 10-20 nm with a $Fe^{2+}$ and/or $Fe^{3+}$ core surrounded by dextran or PEG molecules. Colloidal gold nanoparticles are described in e.g., Qian et. al., Nat. Biotechnol. 26(1):83-90 (2008); U.S. Pat. Nos. 7,060,121; 7,232,474; and U.S. P.G. Pub. No. 2008/0166706. Suitable nanoparticles, and methods for constructing and using multifunctional nanoparticles, are discussed in e.g., Sanvicens and Marco, Trends Biotech., 26(8): 425-433 (2008).

In some instances, the particles are polymeric particles. A number of biocompatible polymers suitable for use in the production of the polymeric particles described herein are known in the art, e.g., poly(lactic-co-glycolic) acid (PLGA), polylactide, and polyglycolide. In a specific embodiment, the polymeric particle comprises a PLGA polymer. In a specific embodiment, the polymeric particle comprises a polylactide polymer. In a specific embodiment, the polymeric particle comprises a polyglycolide polymer.

In some embodiments, the polymeric particles can be poly(ethyleneglycol)ated (PEGylated), e.g., as described in U.S. Pat. Nos. 7,291,598; 5,145,684; 6,270,806; 7,348,030, and others, to reduce blood protein binding, and/or liver and spleen uptake. For example, in some embodiments, the polymeric particle comprises a PEGylated PLGA polymer. In another example, the polymeric particle comprises a PEGylated polylactide polymer. In yet another example, the polymeric particle comprises a PEGylated polyglycolide polymer. PEGylation creates stealth-like structures to bypass immune recognition by macrophage cells, thus achieving suppressed opsonization and enhanced retention of the particles in circulation. Such simple surface modification, e.g., pegylation, can increase the circulation half-life of a particle from several minutes to several or tens of hours.

In some embodiments, the polymeric particles are attached (linked, e.g., covalently conjugated) to an antibody or antigen-binding fragment thereof described herein. The antibody or antigen-binding fragment thereof may be attached to the polymeric particles via functional groups of the polymer of the polymeric nanoparticle. For example, the antibody or antigen-binding fragment thereof may be conjugated to the polymeric particle.

The nano- or microparticles are attached (linked) to an antibody or antigen-binding fragment thereof described herein via a functional group(s). In some embodiments, the nano- or microparticles are associated with a polymer that includes the functional group(s), and also serves to keep the metal oxides dispersed from each other. The polymer can be a synthetic polymer, such as, but not limited to, polyethylene glycol or silane, natural polymers, or derivatives of either synthetic or natural polymers or a combination of these. Useful polymers are hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, carboxydextran, carboxmethyl dextran, and/or reduced carboxymethyl dextran. The metal oxide can be a collection of one or more crystals that contact each other, or that are individually entrapped or surrounded by the polymer.

In other embodiments, the nano- or microparticles are associated with non-polymeric functional group compositions. Methods are known to synthesize stabilized, functionalized nano- or microparticles without associated polymers, which are also within the scope of this invention. Such methods are described, for example, in Halbreich et al., Biochimie, 80 (5-6):379-90, 1998.

In some embodiments, an immunosuppressive or immunoregulatory drug described herein can be encapsulated within, e.g., mixed within or under a coating of, the nano- or microparticles. In some embodiments, an immunosuppressive or immunoregulatory drug described herein can be conjugated with, e.g., outside the surface of, the nano- or microparticles.

i. Immunosuppressive or Immunoregulatory Drugs

Three classical immunosuppressive drugs, Cyclosporine A, Rapamycin, and Tacrolimus have been successfully incorporated into the drug-containing particles described herein, which showed controlled drug release and suppression of T cell activity in vitro (Azzi, J., et al., FASEB J 24: 3927-3938, 2010; Tang, L., et al., J. Transplantation, 2012: 896141, 2012; Tong, R. & Cheng, J. J., Macromolecules 45: 2225-2232, 2012).

In some embodiments, Tacrolimus (also known as TAC, FK-509, or fujimycin) is incorporated into the drug-containing particles described herein. Tacrolimus is an immunosuppressive drug that is mainly used after allogeneic organ transplant to reduce the host's immune responses and lower the risk of organ rejection. At the molecular level, Tacrolimus is a macrolide lactone that can reduce interleukin-2 (IL-2) production by the T-cells (Liu J, Farmer J, Lane W, Friedman J, Weissman I, Schreiber S, Cell 66 (4): 807-815, 1991). Other suitable immunosuppressive or immunoregulatory drugs that can be incorporated into the present delivery system include, but are not limited to, mycophenolate, mofetil, cyclosporine, sirolimus, fingolimod, myriocin, cyclophosphamide, a corticosteroid (e.g., cortisol, corticosterone, cortisone, or aldosterone), rapamycin, mycophenolate, mofetil, checkpoint inhibitors (e.g., anti-CTLA-4 antibodies, anti-PD1 antibodies, anti-PDL1 antibodies), anti-inflammatory agents (e.g., anti-TNF drugs, such as, e.g., adalimumab), chemotherapeutic agents, and monoclonal antibodies such as, e.g., anti-CD3 antibody, anti-CD25 antibody, anti-IL6 antibody, CTLA-4-Ig, adalimumab, anti-CD52 antibody (e.g., alemtuzumab). In some embodiments, taxol is incorporated into the drug-containing particles described herein. In some embodiments, the immunosuppressive or immunoregulatory drugs have one or more hydroxyl groups or thiol groups and can function as polymerization initiators in the presence of certain catalysts.

In some embodiments, the drug is a chemotherapeutic agent. Chemotherapy can be, e.g., using a cytotoxin or cytotoxic agent that is detrimental to cells. Examples include taxol, mitomycin, etoposide, tenoposide, vincristine, vinblastine, colchicin, doxorubicin, daunorubicin, mitoxantrone, mithramycin, actinomycin D, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa, chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). See, e.g., Johnson and Win, Oncoimmunology. 2018 Mar. 13; 7(4):e1408744; Chowdhury et al., J Intern Med. 2018 February; 283(2):110-120; Tang et al., Nature Reviews Drug Discovery 17:854-855 (2018).

ii. Synthesis of Drug-Containing Polymeric Particles

There are a variety of ways that the drug-containing nano- or microparticles can be prepared, but in all methods, the result must be a particle with functional groups that can be used to link the particle to the antibody or antigen-binding fragment thereof described herein.

In some embodiments, an immunosuppressive or immunoregulatory drug described herein can be encapsulated within, e.g., mixed within or under a coating of, the nano- or microparticles. Such drug-encapsulated particles can be synthesized using a nanoprecipitation method, e.g., described in Tang, L., et al., J. Transplantation, 2012: 896141, 2012, the content of which is incorporated by reference herein. Briefly, a drug to be delivered and PEGylated polymers can be dissolved in a suitable organic solvent. The resulting solution can be added dropwise into a nonsolvent, e.g., water, under vigorous stirring to form PEGylated drug-encapsulated polymeric particles. The particle suspension can then be stirred at room temperature to evaporate the organic solvent. An aliquot of the particle suspension can be centrifuged and the supernatant can be analyzed, e.g., by a reverse phase HPLC, to determine the incorporation efficiency and loading of the drug into the particles. The particles can then be purified and collected, e.g., by ultrafiltration. Optionally, a lyoprotectant, e.g., bovine serum albumin (BSA), can be added to the particle solution, which can then be lyophilized and stored at −20° C. The size and polydispersity of the resulting particles can be determined by dynamic light scattering (DLS) and/or scanning electron microscope (SEM).

In some embodiments, an immunosuppressive or immunoregulatory drug described herein can be conjugated with, e.g., outside the surface of, the nano- or microparticles. Such drug-conjugated particles can be synthesized using methods described in e.g., Azzi, J., et al., FASEB J 24: 3927-3938, 2010, or in the international application publication WO 2008/109483, the contents of which are incorporated by reference herein. Briefly, a drug to be delivered can be mixed with one or more cyclic monomers and a catalyst in a suitable solvent. The drug serves as an initiator in a ring-opening polymerization reaction to form drug-polymer conjugates in which the drug is covalently bonded to the polymer. Because the drug is used as the initiator of polymerization, the efficiency of conjugation of the drug to the polymer is very high, and the drug-loading percentage can be controlled by adjusting the monomer/initiator ratio. The drug-polymer conjugates and PEGylated polymers can then be added dropwise into a nonsolvent, e.g., water, under vigorous stirring to form PEGylated drug-conjugated polymeric particles. The particle suspension can then be stirred at room temperature to evaporate the organic solvent. The particles can be purified and collected, e.g., by ultrafiltration. Optionally, a lyoprotectant, e.g., bovine serum albumin (BSA), can be added to the particle solution, which can then be lyophilized and stored at −20° C. The size and polydispersity of the resulting particles can be determined by dynamic light scattering (DLS) and/or scanning electron microscope (SEM).

Suitable monomers for the ring-opening polymerization include various cyclic monomers, e.g., cyclic esters, cyclic carbonates, cyclic siloxanes, cyclic phosphates, cyclic peptides or amino acid derivative, or cyclic phosphazanes. Exemplified cyclic monomers include lactide or glycolide.

The polymeric particles described herein can be used to deliver any small molecule drug that contains at least one functional group capable of initiating the ring-opening polymerization reaction, e.g. a hydroxyl group or a thiol group. The drug may contain a plurality of such polymerization initiation groups, e.g., a plurality of hydroxyl groups or thiol groups. In some embodiments, the drug contains only one of such polymerization groups. The hydroxyl groups may be primary, secondary or tertiary hydroxyl groups. Similarly, the thiol groups may be primary, secondary or tertiary thiol groups. The hydroxyl group may also be a phenolic hydroxyl group. In some embodiments, the drug contains one or more non-phenolic hydroxyl groups. In some embodiments, the drug contains one or more non-phenolic hydroxyl groups that are primary or secondary hydroxyl groups. In some embodiments, the drug contains a single nonphenolic hydroxyl group. In some embodiments, the drug contains a single primary or secondary hydroxyl group. In some embodiments, the immunosuppressive or immunoregulatory drugs having one or more hydroxyl groups or thiol groups function as polymerization initiators in the presence of certain catalysts.

A number of catalysts can be employed to facilitate formation of the drug-containing polymeric particles. Exemplary catalysts include numerous metal-oxides (M-ORs) and alcohol-metal oxides (RO-M) developed for controlled, living polymerization of cyclic monomers (O. Dechy-Cabaret, B. Martin-Vaca, & D. Bourissou, Chemical Reviews 104: 6147-6176, 2004). Metal-oxides can be prepared in situ by mixing a hydroxyl-containing compound with an active metal complex, such as a metal-amido compound (B. M. Chamberlain, M. Cheng, D. R. Moore, T. M. Ovitt, E. B. Lobkovsky, G. W. Coates, J. Am. Chem. Soc. 123: 3229, 2001). For example, (BDI)MgN(TMS)2, a very active catalyst for the polymerization of lactide, can be employed (Chamberlain, 2001). Certain Zn catalysts, e.g., (BDI)ZnN(TMS)2, facilitate fast initiation and relatively slow chain propagation, and can be used as catalyst for the polymerization. Zn-mediated lactide polymerization can result in polymers with narrow polydispersity. Other useful catalysts include Ca and Fe catalysts. Since Mg, Zn, Ca, and Fe are elements found in human body, catalysts containing these elements have a better safety profile than other active catalysts containing Al and Sn. Exemplary Zn, Mg, Ca and Fe catalysts, include the organocatalysts are described in WO 2008/109483. In some embodiments, a Zn catalyst, e.g., (BDI)ZnN(TMS)2, is used to initiate the drug-containing polymeric particles.

The particles described herein have shown high drug loading (about 50%) and loading efficiency (98-100%), well-controlled drug release kinetics without a burst release effect and excellent controlled particle size with a very narrow size distribution (Tong, R. & Cheng, J., Angew. Chem., Int. Ed. 47: 4830-4834, 2008; Tong, R. & Cheng, J., J. Am. Chem. Soc. 131: 4744-4754, 2009).

Particle size can be controlled by adjusting reaction conditions, for example, by varying temperature as described in U.S. Pat. No. 5,262,176. Uniform particle size materials can also be made by fractionating the particles using centrifugation, ultrafiltration, or gel filtration, as described, for example in U.S. Pat. No. 5,492,814.

The size of the drug-containing polymeric particles described herein can range from about 2 nm to about 500 µm. In some embodiments, the drug-containing polymer particles have an overall size ranging from about 0.01 µm to about 10 µm, e.g., about 0.05 µm to about 5 µm, about 0.1 µm to about 3 µm, about 1 µm to about 2.5 µm. In some embodiments, the drug-containing polymeric particles have an overall size ranging from about 500 nm to about 5 µm. In some embodiments, the drug-containing polymeric particles have an overall size ranging from about 1 µm to about 2.5 µm. In some embodiments, the drug-containing polymeric particles have an overall size ranging from about 200 nm to about 800 nm. In some embodiments, the drug-containing polymeric particles have an overall size in the 2-20 nm range and are particularly useful for delivery to cells.

In some embodiments, the drug-containing polymeric particles disclosed herein can be surface-modified to provide functional groups that can be used to link the particles to an antibody or antigen-binding fragment thereof described herein. For example, the particles can be functionalized according to a version of the method of Albrecht et al., Biochimie, 80(5-6): 379-90, 1998. Dimercapto-succinic acid can be coupled to the particles and provides a carboxyl functional group. By functionalized is meant the presence of amino or carboxyl or other reactive groups that can be used to attach desired moieties to the particles.

Carboxyl functionalized nano- or microparticles can be made, for example, according to the method of Gorman (see WO 00/61191). Carboxyl-functionalized particles can also be made from polysaccharide coated particles by reaction with bromo or chloroacetic acid in strong base to attach carboxyl groups. In addition, carboxyl-functionalized particles can be made from amino-functionalized particles by converting amino to carboxyl groups by the use of reagents such as succinic anhydride or maleic anhydride.

Particles can also be treated with periodate to form aldehyde groups. The aldehyde-containing particles can then be reacted with a diamine (e.g., ethylene diamine or hexanediamine), which will form a Schiff base, followed by reduction with sodium borohydride or sodium cyanoborohydride.

Dextran-coated particles can also be made and cross-linked, e.g., with epichlorohydrin. The addition of ammonia will react with epoxy groups to generate amine groups, see Hogemann et al., Bioconjug. Chem. 2000. 11(6):941-6, and Josephson et al., Bioconjug. Chem., 1999, 10(2):186-91.

Carboxyl-functionalized particles can be converted to amino-functionalized magnetic particles by the use of water-soluble carbodiimides and diamines such as ethylene diamine or hexane diamine.

Avidin or streptavidin can be attached to particles for use with a biotinylated binding moiety, such as an oligonucleotide or polypeptide. See e.g., Shen et al., Bioconjug. Chem., 1996, 7(3):311-6. Similarly, biotin can be attached to a particle for use with an avidin-labeled binding moiety.

In some embodiments, the drug-containing polymeric particles can be pegylated, e.g., as described in U.S. Pat. Nos. 7,291,598; 5,145,684; 6,270,806; 7,348,030, and others, to reduce blood protein binding, and/or liver and spleen uptake. Pegylation creates stealth-like structures to bypass immune recognition by macrophage cells, thus achieving suppressed opsonization and enhanced retention of the particles in circulation. Such simple surface modification, e.g., pegylation, can increase the circulation half-life of a particle from several minutes to several or tens of hours.

iii. Methods of Conjugation

The drug-containing polymeric particles described herein are conjugated with an antibody or antigen-binding fragment thereof described herein.

In some embodiments, the antibody or antigen-binding fragment thereof can be linked to the drug-containing polymeric particles through covalent attachment, e.g., through a chemical bond between a functional group on the molecule and a functional group on the drug-containing polymeric particles. A functional group can be an amino or carboxyl or other reactive groups that can be used to attach desired moieties to the particles, e.g., the antibody or antigen-binding fragment thereof.

In some embodiments, antibody or antigen-binding fragment thereof described herein can be attached to the drug-containing polymeric particles via a linker or binding agent. The linker or binding agent can have terminal amino, carboxy, sulfhydryl, or phosphate groups. Illustrative examples of useful linkers or binding agents include organic polymers, e.g., polyethylene glycol (PEG) and derivatives thereof, proteins, and small molecules.

VI. Methods of Use

As described above, the present disclosure is based, at least in part, on the development of an anti-PNAd antibody having improved binding affinity to cells expressing PNAd (Example 6) and improved ability to block T cell homing to lymph nodes (Example 4). Administration of drug conjugated to anti-PNAd antibody described herein resulted in reduced tumor growth, reduced tumor metastasis, and reduced tumor-draining lymph node fibrosis (Example 7), in addition to increased survival time (Example 8). Moreover, administration of drug conjugated to anti-PNAd antibody described herein also increased survival time after heart transplantation (Example 9). Thus, the antibody-drug conjugates described herein and in the Examples below may be used to treat the primary tumor and local metastasis in lymph nodes and distant metastasis; this use of the antibody was not expected because it was not known that the metastatic lesions express HEV. Accordingly, the present disclosure provides compositions and methods for suppressing a lymphocyte-mediated immune response in a subject in need thereof, treating or delaying progression of autoimmune diabetes in a subject in need thereof, treating lymphocyte-mediated inflammation in a subject in need thereof, and treating or reducing the metastasis of a peripheral lymph node addressin (PNAd)-expressing malignancy in a subject in need thereof. These methods can include identifying a subject in need of treatment and administering to the subject one or more of the compositions described herein. A subject in need of treatment can be identified, e.g., by a medical practitioner. In some embodiments, the antibodies or antigen-binding fragments thereof described herein (or a composition or particle (e.g., drug-containing particle) comprising the antibody or antigen-binding fragment thereof) may be used in a method of suppressing a lymphocyte-mediated immune response in a subject in need thereof, comprising administering to the subject a therapeutically effective amount of the antibodies or antigen-binding fragments thereof described herein (or a composition or particle (e.g., drug-containing particle) comprising the antibody or antigen-binding fragment thereof). In some embodiments, the antibodies or antigen-binding fragments thereof described herein (or a composition or particle (e.g., drug-containing particle) comprising the antibody or antigen-binding fragment thereof) may be used in a method of treating or delaying progression of autoimmune diabetes in a subject in need thereof, administering to the subject a therapeutically effective amount of the antibodies or antigen-binding fragments thereof described herein (or a composition or particle (e.g., drug-containing particle) comprising the antibody or antigen-binding fragment thereof). In some embodiments, the antibodies or antigen-binding fragments thereof described herein (or a composition or particle (e.g., drug-containing particle) comprising the antibody or antigen-binding fragment thereof) may be used in a method of treating lymphocyte-mediated inflammation in a subject in need thereof, the method comprising administering to the subject a therapeutically effective amount of the antibodies or antigen-binding fragments thereof described herein (or a composition or particle (e.g., drug-containing particle) comprising the antibody or antigen-binding fragment thereof). In some embodiments, the antibodies or antigen-binding fragments thereof described herein (or a composition or particle (e.g., drug-containing particle) comprising the antibody or antigen-binding fragment thereof) may be used in a method of treating or reducing the metastasis of a PNAd-expressing malignancy in a subject in need thereof, the method comprising administering to the subject a therapeutically effective amount of the antibodies or antigen-binding fragments thereof described herein (or a composition or particle (e.g., drug-containing particle) comprising the antibody or antigen-binding fragment thereof). In some embodiments, the PNAd-expressing malignancy is lymphoma. In some embodiments, the PNAd-expressing malignancy is cancer. In some instances, the cancer is breast cancer. In some instances, the cancer is a primary tumor. In some instances, the cancer is a local metastasis. In some instances, the cancer is a local metastasis in lymph nodes. In some instances, the cancer is a distant metastasis (i.e., distant from the location of the primary tumor).

As described above, the antibodies and antigen-binding fragments thereof described herein are particularly useful in the development of drug-containing polymeric particles that mimic lymphocyte migration in vivo and can specifically deliver drugs, e.g., immunosuppressive or immunoregulatory drugs to lymphoid tissues and sites of chronic inflammation where T-cell activation and T-cell mediated injury are occurring. Accordingly, the present disclosure provides compositions and methods for treating, or delaying disease progression in a subject (e.g., a human) in need of immune suppression, e.g., for autoimmune or inflammatory disorders such as type 1 diabetes or rheumatoid arthritis; and immune suppression following transplantation, e.g., in cardiac or other organ transplantation. The present disclosure also provides compositions and methods for treating, or delaying disease progression in a subject (e.g., a human) who has a cancer (e.g., a lymphoma or breast cancer). The present disclosure also provides methods of treating, or delaying progression of malignancies, such as cancers, e.g., lymphomas, where the lymphocyte homing process plays a role in the dissemination of the tumor, and/or wherein the malignancy expresses PNAd by delivering chemotherapy drugs to lymphoid tissues.

These methods can include identifying a subject in need of treatment and administering to the subject one or more of the compositions described herein. A subject in need of treatment can be identified, e.g., by a medical practitioner.

A. Methods of Treating Autoimmune Diabetes

Type 1 diabetes (T1D) is characterized by the autoimmune destruction of insulin-producing 13 cells of the pancreatic islets by autoreactive T cells (Hoglund, P., et al., J Exp Med 189: 331-339, 1999). Central to the pathogenesis of autoimmune diabetes is the presentation of islet antigens by antigen-presenting cells in the draining pancreatic lymph nodes to T cells, resulting in the activation of autoreactive T cells (Roncarolo, M. G. & Battaglia, M., Nat Rev Immunol 7: 585-598, 2007). A number of studies indicate the pancreatic lymph nodes play critical roles in the pathogenesis of autoimmune diabetes (Katz, J. D., Wang, B., Haskins, K., Benoist, C. & Mathis, D. Cell 74: 1089-1100, 1993; Hoglund, P., et al., J Exp Med 189, 331-339, 1999; Turley, S., Poirot, L., Hattori, M., Benoist, C. & Mathis, D., J Exp Med 198: 1527-1537, 2003; Turley, S. J., Lee, J. W., Dutton-Swain, N., Mathis, D. & Benoist, C., Proc Natl Acad Sci USA 102: 17729-17733, 2005). Following priming, activated autoreactive T cells are then recruited to the pancreas causing insulitis.

The PNAd pathway has been shown to regulate lymphocyte trafficking to lymphoid tissue in NOD mice (Hanninen, A., Salmi, M., Simell, O., Andrew, D. & Jalkanen, S., Blood 88: 934-944, 1996; Xu, B., et al., J Exp Med 197: 1255-1267, 2003; Xu, B., Cook, R. E. & Michie, S. A., J Autoimmun. 35: 124-129, 2010). Moreover, PNAd is upregulated on venous endothelium in inflammatory states and autoimmune diseases such as T1D (Michie, S. A., Streeter, P. R., Bolt, P. A., Butcher, E. C. & Picker, L. J., Am J Pathol 143: 1688-1698, 1993; Mikulowska-Mennis, A., Xu, B., Berberian, J. M. & Michie, S. A., Am J Pathol 159: 671-681, 2001; Penaranda, C. & Bluestone, J. A., Immunity 31: 534-536, 2009). Inflammatory signals and endothelial cell activation during insulitis have been reported to render islet endothelial morphology and characteristics to HEVs expressing PNAd. Therefore, the onset of insulitis is reported to be associated with islet expression of PNAd (Hanninen, A., Salmi, M., Simell, O., Andrew, D. & Jalkanen, S., Blood 88, 934-944, 1996; Faveeuw, C., Gagnerault, M. C., Kraal, G. & Lepault, F., Int Immunol 7: 1905-1913, 1995; Yang, X. D., et al., Proc Natl Acad Sci USA 91: 12604-12608, 1994; Yang, X. D., et al., J Autoimmun 7: 859-864, 1994; Faveeuw, C., Gagnerault, M. C. & Lepault, F., J Immunol 152: 5969-5978, 1994; Hanninen, A., Salmi, M., Simell, 0. & Jalkanen, S., Diabetes 45: 1173-1180, 1996; Dong, H., Burke, S. D. & Croy, B. A., Placenta 29: 201-209, 2008). The interaction of leukocytes with endothelial cells via adhesion molecules affords great opportunity to design various strategies such as developing inhibitors or antibodies that target the trafficking of leukocytes (Mackay, C. R., Nat Immunol 9: 988-998, 2008).

The antibodies or antigen-binding fragments thereof, or conjugates thereof described herein, can be used to selectively deliver immunosuppressant to the pancreatic lymph nodes and pancreas to efficiently suppress autoreactive T cells and to treat or delay progression of autoimmune diabetes such as type 1 diabetes (T1D). A subject who has some pancreatic β cell function is more likely to benefit from the present method of treatment. Such a subject can be identified, e.g., by determining the C-peptide level in the subject is above a threshold.

B. Immune Suppression After Transplantation

After tissue or organ transplantation, immune cells are activated against exogenous antigens present on the allografts. The activated immune cells can travel to the transplanted tissue or organ and cause damages there. Delivery of a small amount of immunosuppressive drugs directly to the sites where immune cells are activated can reduce their activation and increase allograft survival. Such targeted delivery of immunosuppressive drugs also reduces toxicity seen in systemic administration of a large amount of immunosuppressive medications. The compositions described herein are useful vehicles to deliver immunosuppressant directly to the sites of organ transplantation and increase allograft survival.

C. Methods of Treating Lymphomas

The compositions described herein can also be used to treat lymphomas, e.g., PNAd-expressing lymphomas. Lymphocyte homing process is known to play a role in the dissemination of some tumors. For example, the dissemination of non-Hodgkin lymphomas (NHLs) is mediated by lymphocyte homing program (Pals S. T., de Gorter D. J. J., and Spaargaren M, Blood 110(9): 3102-3111, 2007). Other exemplary lymphomas that can be treated by the compositions disclosed herein include small-lymphocytic lymphoma (SLL), chronic lymphocytic leukemia (CLL), mantle-cell lymphoma (MCL), Burkitt lymphoma (BL), diffuse large B-cell lymphomas (DLBCL), cutaneous lymphomas, e.g., cutaneous T cell lymphoma (CTCL), intestinal lymphomas, e.g., intestinal T-cell lymphomas (ITLs), nodal T-cell lymphomas, extranodal lymphomas arising in the gut-associated lymphoid tissues or the skin, adult T-cell leukemia/lymphoma (ATLL), and B-cell lymphomas of the mucosa-associated lymphoid tissues (MALTs), primary follicular lymphomas (FLs), B-cell chronic lymphocytic leukemia (B-CLL), and hairy-cell leukemia (HCL).

In some embodiments, the antibody or antigen-binding fragment thereof conjugates described herein can be used to treat or delay progression of PNAd-expressing lymphomas.

VII. Pharmaceutical Compositions

A therapeutically effective amount of one or more of the antibodies or antigen binding fragments thereof, or conjugates thereof, described herein can be incorporated into pharmaceutical compositions suitable for administration to a subject, e.g., a human. Such compositions typically include the antibody or antigen binding fragment thereof, or conjugate thereof and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions described herein. Supplementary active compounds can also be incorporated into the compositions, e.g., an inhibitor of degradation of the ligand.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (polyethoxylated castor oil; BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the composition (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL™ (sodium carboxymethyl starch), or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the active compounds (e.g., the antibody or antigen binding fragment thereof, or conjugate thereof) are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration. In one aspect, the pharmaceutical compositions can be included as a part of a kit.

Generally the dosage used to administer a pharmaceutical composition facilitates an intended purpose for prophylaxis and/or treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: "Remington's Pharmaceutical Sciences", 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

VIII. Administration

A therapeutically effective amount of one or more of the compositions described herein can be administered by standard methods, for example, by one or more routes of administration, e.g., by one or more of the routes of administration currently approved by the United States Food and Drug Administration (FDA; see, for example world wide web address fda.gov/cder/dsm/DRG/drg00301.htm), e.g., orally, topically, mucosally, or parenterally, e.g., intravenously or intramuscularly.

IX. Kits

The present invention also includes kits for use in a method described herein. In some embodiments, the kits comprise one or more doses of a composition described herein. The composition, shape, and type of dosage form for the induction regimen and maintenance regimen may vary depending on a subject's requirements. For example, dosage form may be a parenteral dosage form, an oral dosage form, a delayed or controlled release dosage form, a topical, and a mucosal dosage form, including any combination thereof.

In a particular embodiment, a kit can contain one or more of the following in a package or container: (1) one or more doses of a composition described herein; (2) one or more pharmaceutically acceptable adjuvants or excipients (e.g., a pharmaceutically acceptable salt, solvate, hydrate, stereoisomer, or clathrate); (3) one or more vehicles for administration of the dose; (5) instructions for administration. Embodiments in which two or more, including all, of the components (1)-(5), are found in the same container can also be used.

When a kit is supplied, the different components of the compositions included can be packaged in separate containers and admixed immediately before use. Such packaging of the components separately can permit long term storage without losing the active components' functions. When more than one bioactive agent (e.g., an antibody or antigen-binding fragment thereof or conjugate thereof) is included in a particular kit, the bioactive agents may be (1) packaged separately and admixed separately with appropriate (similar of different, but compatible) adjuvants or excipients immediately before use, (2) packaged together and admixed together immediately before use, or (3) packaged separately and admixed together immediately before use. If the chosen compounds (e.g., an antibody or antigen-binding fragment thereof or conjugate thereof) will remain stable after admixing, the compounds may be admixed at a time before use other than immediately before use, including, for example, minutes, hours, days, months, years, and at the time of manufacture.

The compositions included in particular kits of the present invention can be supplied in containers of any sort such that the life of the different components are optimally preserved and are not adsorbed or altered by the materials of the container. Suitable materials for these containers may include, for example, glass, organic polymers (e.g., polycarbonate and polystyrene), ceramic, metal (e.g., aluminum), an alloy, or any other material typically employed to hold similar reagents. Exemplary containers can include, without limitation, test tubes, vials, flasks, bottles, syringes, and the like.

As stated above, the kits can also be supplied with instructional materials. These instructions may be printed and/or may be supplied, without limitation, as an electronic-readable medium, such as a floppy disc, a CD-ROM, a DVD, a Zip disc, a video cassette, an audiotape, and a flash memory device. Alternatively, instructions may be published on an internet web site or may be distributed to the user as an electronic mail.

EXAMPLES

The invention is further described in the following examples, which do not limit the scope of the invention described in the claims.

Example 1: MHA112 Monoclonal Antibody (mAb) Recognizes HEVs in Mice and Human

Figure 1A:
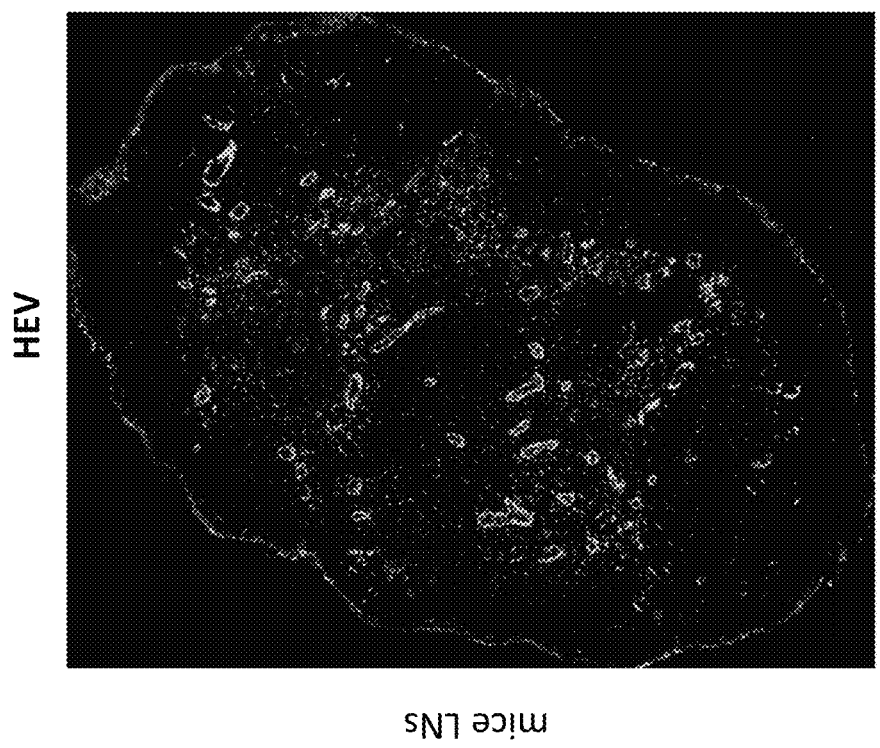

Two of GlcNAc6ST1/2/4 triple knock-out (KO) mice, which lack the peripheral lymph node vascular addressin (PNAd), were immunized with Chinese hamster ovary (CHO) cell lines expressing CD34 decorated with sialyl Lewis$^X$ (sLeX)-type glycans. MHA112 single hybridoma clone was identified by HEV immunofluorescence staining. The supernatant of MHA112 hybridoma culture was collected and used to stain mice lymph nodes (LNs) and human tonsil section. FIG. 1A shows a low-magnification image of high endothelial venule (HEV) structure of mice LNs, which was recognized by MHA112 hybridoma supernatant. Higher magnification images (FIG. 1B) demonstrated that MHA112 stained mice and human HEVs structure.

Example 2: MHA112 mAb Isotyping

Figure 2:
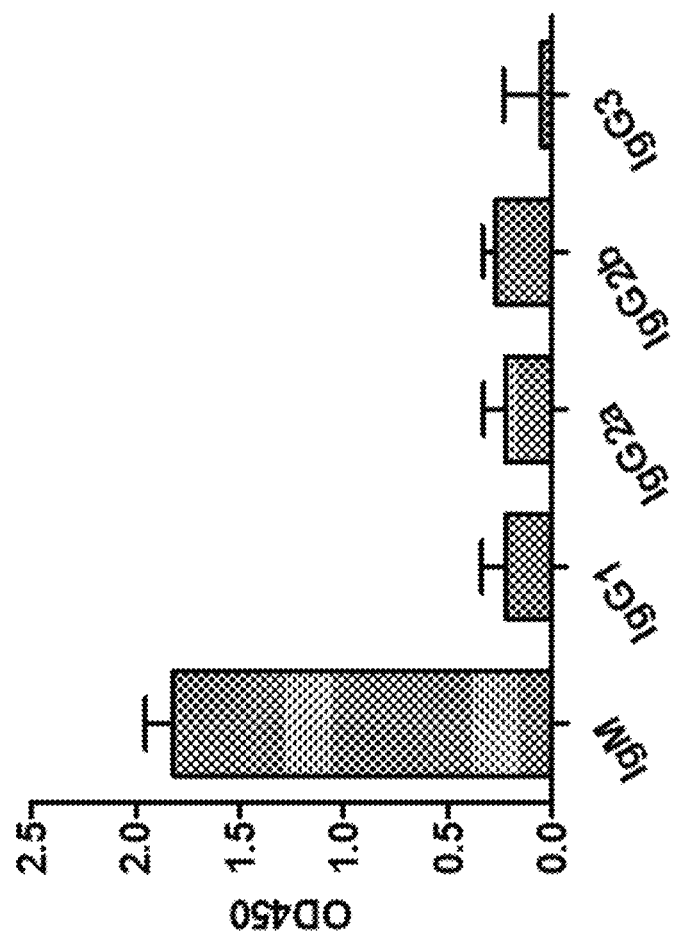
FIG. 2: MHA112 mAb isotyping. MHA112 mAb isotype was determined by isotyping enzyme-linked immunosorbent assay (ELISA). The absorbance was recorded at 450 nm.

Next, isotyping enzyme-linked immunosorbent assay (ELISA) was performed to identify the immunoglobulin (Ig) form of MHA112 mAb. As it is shown in FIG. 2A, MHA112 supernatant was positive in anti-IgM coated well. These data indicated MHA112 isotype is mouse IgM.

Example 3: Trafficking of MHA112 mAb Conjugated NP to the LN

MECA79 is a monoclonal antibody that recognizes all known L-selectin ligands on endothelial venules—PNAds, including CD34, GlyCAM-1, and a subset of MAdCAM-1 (Hemmerich, S., Butcher, E. C. & Rosen, S. D., J Exp Med 180, 2219-2226, 1994). MECA79 was produced by using collagenase-dispersed mesenteric and peripheral lymph node stromal elements as immunogen and selected based on selective staining of peripheral lymph node HEV (Streeter et al., J. Cell. Biol. 107:1853-1862, 1988).

Figure 3A:
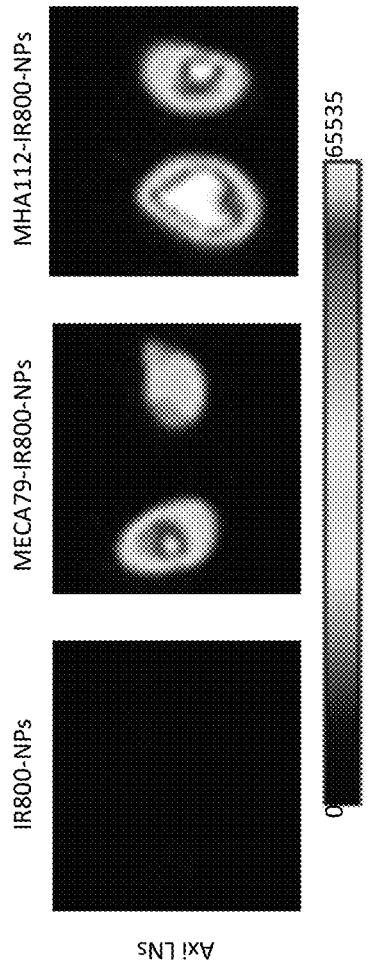
FIG. 3A-B: Trafficking of MHA112 mAb conjugated nanoparticle (NP) to the LNs.
Figure 3B:
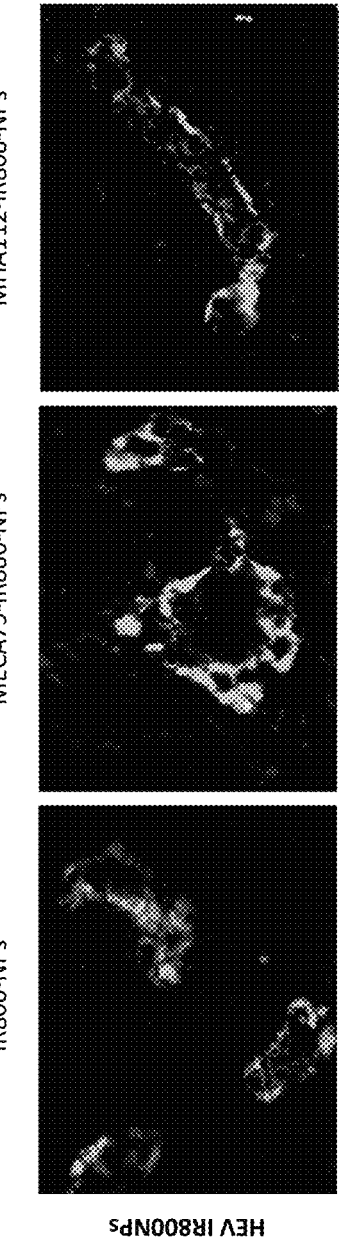

MHA112-conjugated, MECA79-conjugated and non-conjugated particles (loaded with IR800 dye) were injected intravenously into mice. Twenty-four hours post-injection analysis showed high signal in the LNs of MHA112-NPs and positive control MECA79-NPs groups, as compared to the mice injected with non-conjugated IR800-NPs (FIG. 3A). The sections of Axillary LN were then stained to assess the intra-LN distribution of NP at 24 hours post-injection. Cell nuclei were stained blue with DAPI (4',6-diamidino-2-phylindole). PNAd was stained green using MECA79 mAb and NPs were visualized in red. MECA79-NPs and MHA112-NPs were localized around HEVs in 24 hours. Significantly fewer NPs were detected in the LN of the mice injected with non-targeted NPs (FIG. 3B). The trafficking of MHA112-NPs to the LN was comparable with MECA79-NPs, highlighting the specificity of MHA112 mAb in effectively trafficking NPs to the LN.

Example 4: MHA112 mAb Blocked T Cell Homing to LNs

Figure 4:
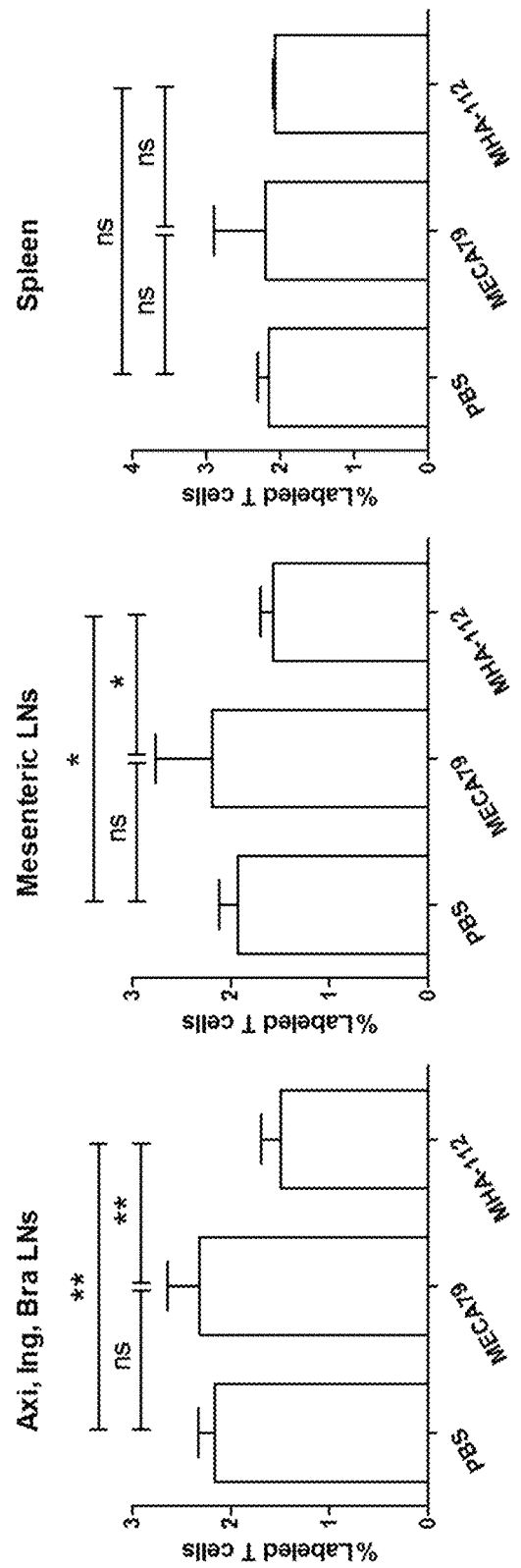
FIG. 4: MHA112 mAb, but not MECA79 mAb, blocked T cell homing to LNs Flow cytometry profiling of labeled T cells homing to LNs in control (PBS, MECA79) and MHA112 mAb treatment groups. Data from three mice/group (n=3) indicated the change of labeled T cells percentages and were summarized in bar chart. *p<0.05, p<0.01, *p<0.001, t-test. n.s.: not significant.

To test whether MHA112 mAb can block T cells homing to LNs in vivo, T cells were labeled with fluorescein isothiocyanate (FITC) florescence dye and transferred into naïve mice, and their distribution assessed 19 hours later. MHA112 (anti-HEVs) reduced the number of transferred T cells that entered Axillary (Axi), Inguinal (Ing) and Brachial (Bra) LN by over 25% (FIG. 4). Moreover, the number of T cells that entered mesenteric LNs in the presence of MHA112 was also reduced by around 12% of PBS controls (FIG. 4). In contrast, MECA79 did not reduce the number of transferred T cells that entered the Axillary, Inguinal, Brachial, or Mesenteric LNs (FIG. 4). Labeled T cells that entered spleen were not changed in three groups (FIG. 4). These data indicated that MHA112 mAb might share the binding site with T cells in HEVs and blocked T cells homing in vivo. MHA112 mAb was significantly better at blocking T cell homing as compared to MECA79 antibody.

Example 5: MHA112 mAb Sequence

The sequences of MHA112 heavy chain and light chain variable regions (VH and VL, respectively) are shown in FIG. 5 and the framework regions (FR1-FR4) and IMGT complementarity determining regions (CDR1-CDR3) are delineated.

Materials and Methods Used in Examples 1 to 5

Immunization and Antibody Isolation

Two of GlcNAc6ST1/2/4 triple KO mice, which lack the PNAd, were immunized with CHO cell lines expressing CD34 decorated with sLeX-type glycans. After the 3rd immunization, mice were sacrificed for hybridoma. Around 500 single clones were screened by HEV staining. Monoclonal antibody MHA112 against mice and human HEV was identified.

Immunohistochemistry

Fresh LNs were embedded in tissue-freezing medium. Cryostat sections (8 μm thick) were cut for imaging by fluorescence confocal microscopy. MHA112 was used for tissue staining as primary antibody. Alexa Fluor 488-conjugated anti-mouse IgM was used as secondary antibody. DAPI was used to stain the cell nuclei.

ELISA

A 96-well ELISA plate was coated with goat anti-mouse IgM, IgG1, IgG2a, IgG2b, IgG3 (5 μg/mL) and incubated overnight at 4° C. Next, the wells were blocked with 5% BSA in Dulbecco's phosphate-buffered saline (DPBS) and washed with DPBS+0.05% Tween-20 (PBST) three times. Then, MHA112 hybridoma supernatant (1:500) was added to the wells for an incubation period of 1 hour at 37° C. The wells were again washed with PBST and incubated with horseradish peroxidase (HRP)-conjugated goat anti-mouse immunoglobulin (Ig) (Invitrogen) for 1 hour at 37° C. After three washes with PBST, the samples were then treated with 3,3',5,5'-tetramethylbenzidine, and absorbance was recorded using a VersaMax microplate reader (Molecular Devices Corp.) at 450 nm.

Lymph Nodes Trafficking

MECA79 and MHA112 mAbs were conjugated to the functional surface of nanoparticles (NPs) using thiol-maleimide chemistry. MECA79 and MHA112 mAbs were pretreated with a mild reducing agent (tris(2-carboxythyl)phosphine (TCEP), 15 minutes, room temperature) to cleave thiol groups and was immediately mixed with NPs suspension. Maleimide groups on NPs covalently conjugate to the cleaved thiol of MECA79 and MHA112 antibodies. The MECA79-NPs and MHA112-NPs were stored at 4° C. prior to use. 8-10 weeks old C57BL/6J (JAX #000664) mice were used for biodistribution studies. The samples were administered intravenously via retro-orbital injection. Trafficking of fluorescent MECA79-IR-NPs and MHA112-IR-NPs were studied using a UVP iBOX Explorer Imaging Microscope (UVP) equipped with 750-780 nm excitation filter and 800 nm long pass emission filter. Several LNs including axillary, brachial, inguinal, renal, and mesenteric were harvested and imaged using the iBOX.

T Cells Blocking

Spleens were harvested from three C57BL/6 mice. Single cell suspensions were prepared, and cells were positively enriched for T cells with MACS reagents and columns (Miltenyi Biotech, Bergisch Gladbach, Germany) according to the manufacturer's instructions. For injection, T cells were labeled with CellTracker Green (Thermo Fisher) and resuspended in sterile saline, and 5 million T cells were injected in 100 μl each mouse. Blocking antibodies MHA112 and MECA79 were administered intraperitoneally (i.p.) at 200 μg in 200 μl per mouse 2 hours before T cell injection. 19 hours after transfer, mice were euthanized and LNs were processed for flow cytometry.

Example 6: MHA112 Binding Affinity

Figure 6:
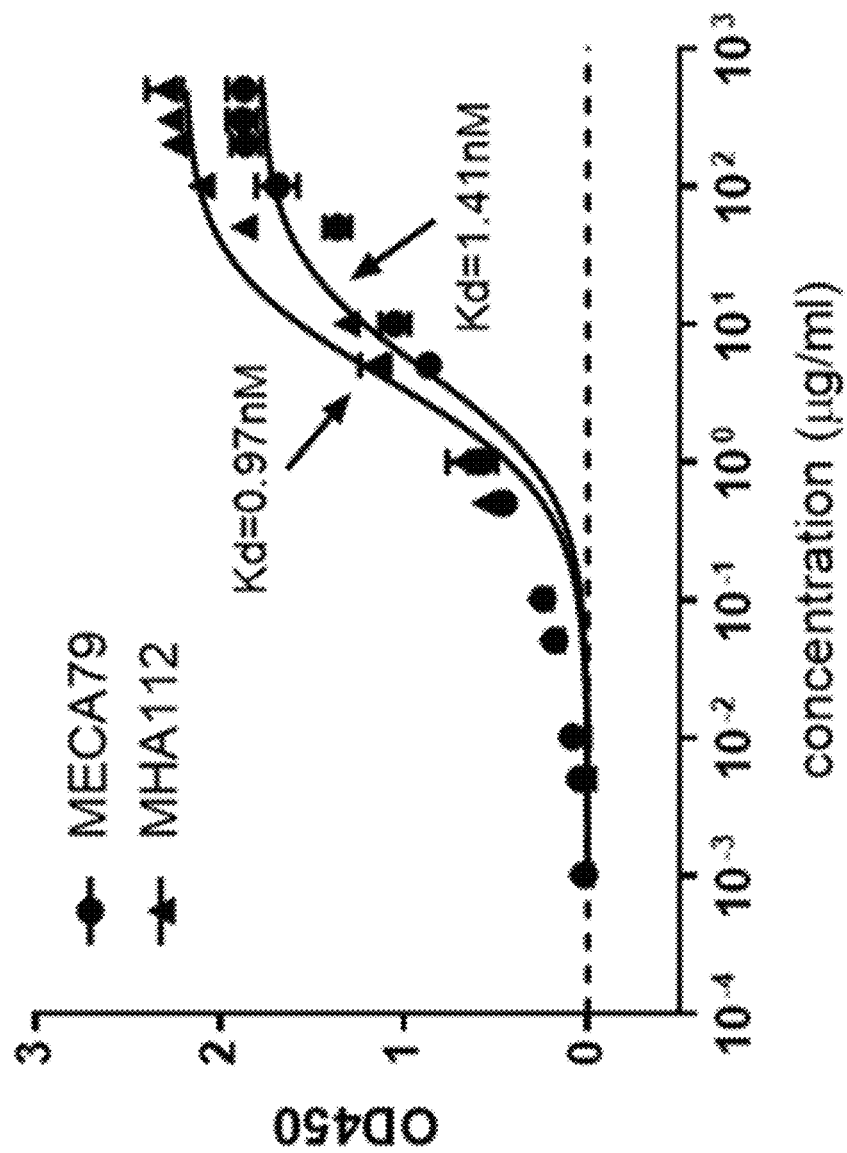
FIG. 6: Determination of binding affinity of MECA79 and MHA112 mAb by ELISA. Different concentrations of MECA79 and MHA112 were tested against CHO-PNAd cells. Kd was calculated. MHA112 was found to have a better binding affinity than the MECA79.

To compare the affinity of MHA112 with MECA79, cell-based ELISA was performed. CHO cells expressing PNAd (CHO-PNAd) ($2\times10^4$) were coated onto 96-well plates and incubated overnight at 37° C. After five washes with phosphate buffered saline (PBS), the plates were fixed with 1% paraformaldehyde (PFA) and blocked with 3% bovine serum albumin (BSA). MECA79 and MHA112 were serially diluted from 1 ng/ml to 300 μg/ml. After five washes in PBST, horseradish peroxidase-(HRP-)conjugated goat anti-mouse and anti-rat secondary antibodies were added at a 1:10,000 dilution and incubated for 1 hour at room temperature. Binding was detected with the addition of TMB (3,3',5,5'-tetramethylbenzidine) substrate, and the reaction was stopped by adding TMB Stop Solution (N600, Thermo Scientific). Absorbance signals were read at 450 nm. As shown in FIG. 6, fitting curves for the binding affinities of MECA79 and MHA112 were constructed, and the Kd values were 1.41 nM and 0.97 nM, respectively. This data indicated that the binding affinity of MHA112 was higher (30%) than MECA79 (FIG. 6).

Figure 7:
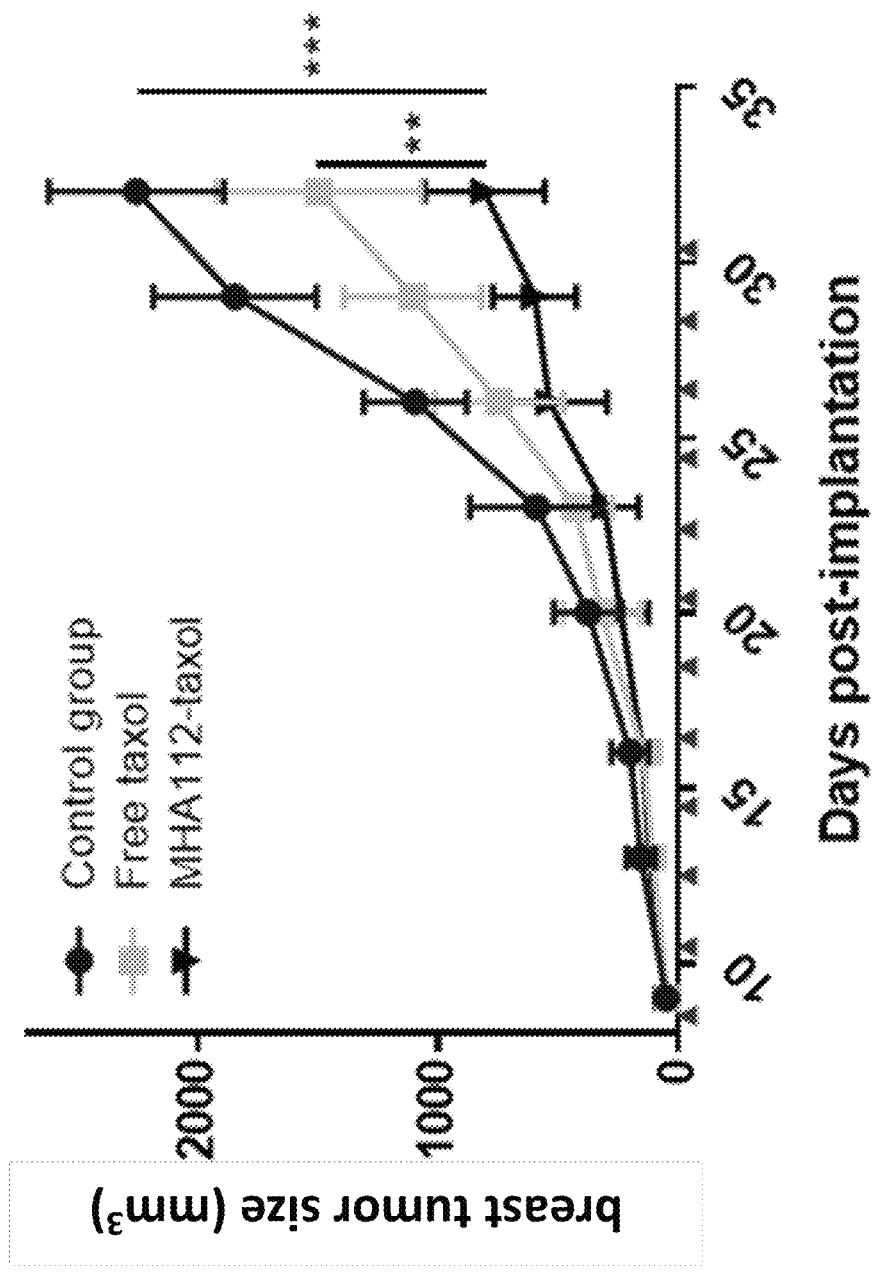
FIG. 7: Breast tumor growth curve demonstrates significantly slower growth of 4T1 mouse breast tumors in the BALB/c-WT mice treated with free taxol and MHA112-taxol (equal to 160 ng free taxol i.v. every two days for 33 days following implantation) (n=12) than the control group treated with PBS (n=12). Data are expressed as means+/−SD. P<0.01, *P<0.001. Triangles on x-axis indicate the injection points. MHA112-taxol group had significantly smaller size tumor as compared to the free Taxol and untreated groups.

Example 7: MHA112-Drug Conjugation Reduce Tumor Growth, Fibrosis, and Metastasis Mice were anesthetized with isoflurane and underwent subcutaneous injection with 4T1 breast tumor cells in the mammary glands ($1\times10^5$ cells per mouse). Starting at 9 days post-implantation, free Taxol or MHA112-Taxol were administered every other day intraperitoneally for 24 days. Tumor growth was monitored two times per week by digital caliper. The tumor size of MHA112-Taxol group was ~3-fold and ~2-fold smaller (p=0.0001) than the control group (phosphate-buffered saline-treatment) and free Taxol group at 5 weeks post-implantation, respectively (FIG. 7). These results showed the superiority of MHA112-Taxol in treating murine model of breast tumors. The kinetics of drug delivery in LN is largely unknown. Draining lymph nodes are the primary sites of metastasis. These metastatic loci in the lymph nodes are extremely difficult to treat with even high does systemic administration of chemotherapy drugs, which often result in significant toxicity and intolerance on patients' part.

Figure 8:
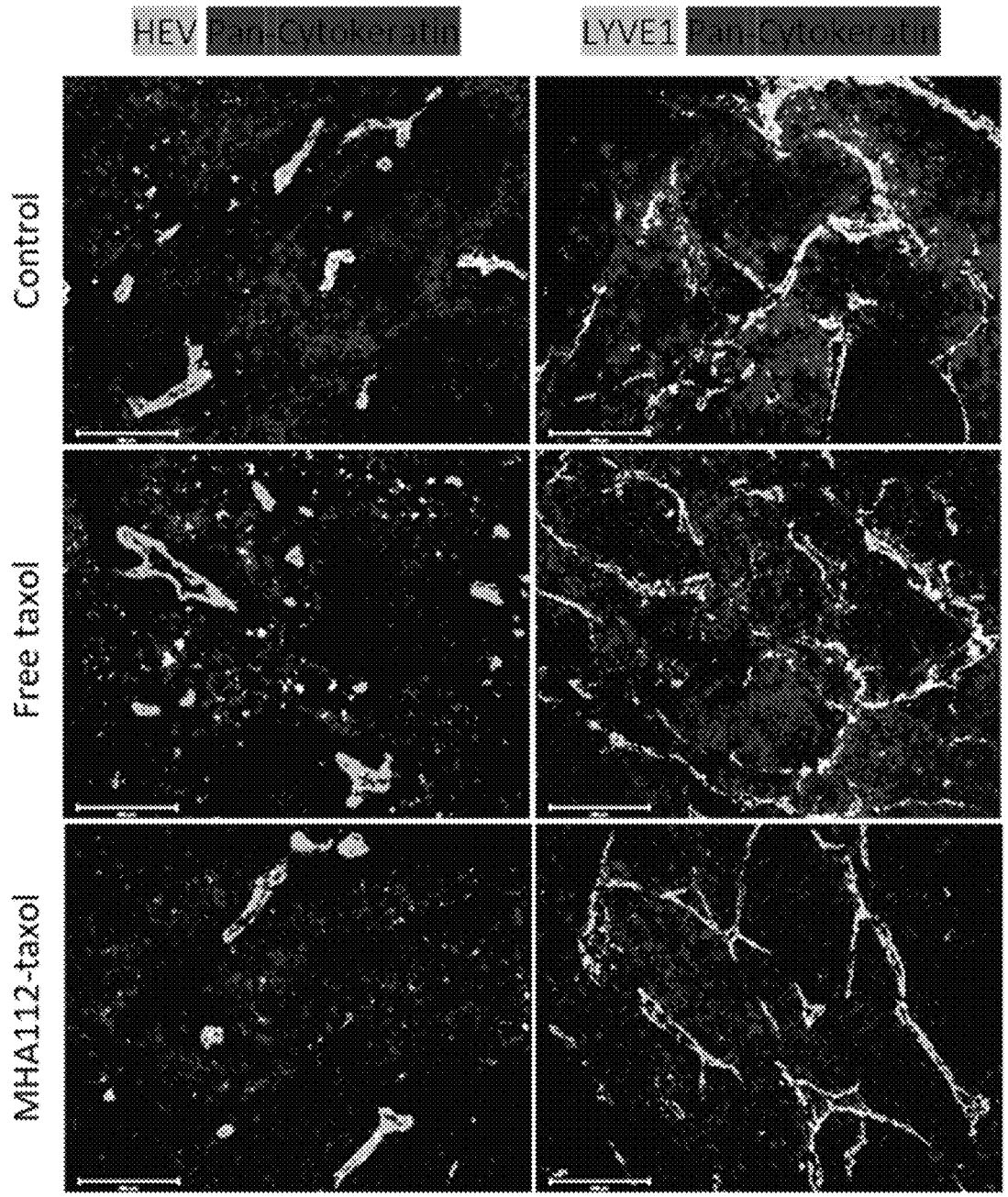
FIG. 8: Fluorescence micrographs of breast tumor draining lymph nodes (DLNs) show that HEVs and LYVE1+ lymphatic vessels (green) are less expanded in the MHA112-taxol group than the control or free taxol group. Pan-Cytokeratin (red) indicates 4T1 metastases in the TDLNs. Scale bar: 100 µm. MHA112-taxol group showed significantly less tumor metastatic as well as lymphatic expansion as compared to the free Taxol and untreated groups.
Figure 9:
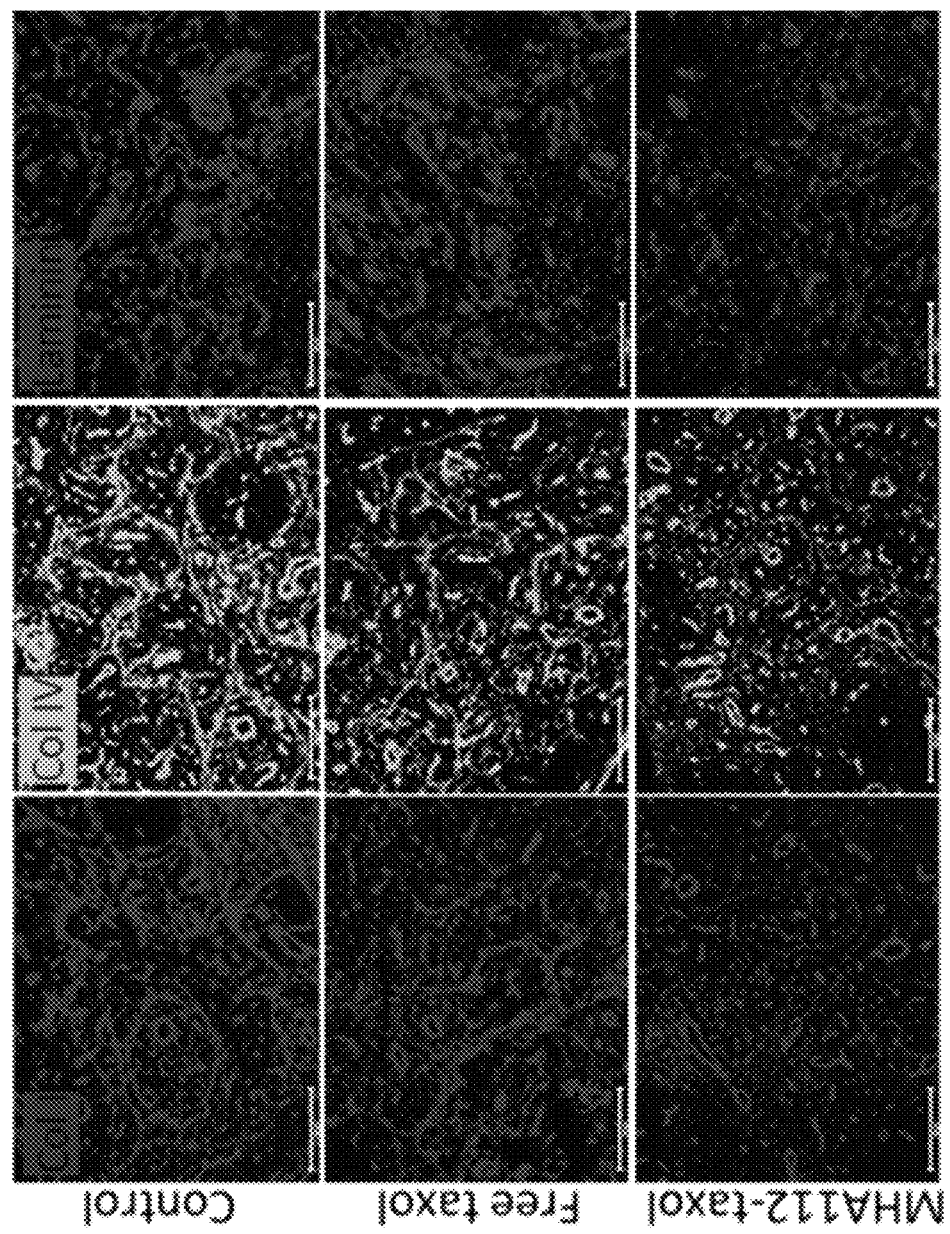
FIG. 9: Fluorescence micrographs of breast tumor DLNs indicate less severe fibrosis (as indicated by collagen I, collagen IV and laminin) in MHA112-taxol group than the control or free taxol group. Scale bar: 100 µm. MHA112-taxol group showed significantly less lymph node fibrosis as compared to the free Taxol and untreated groups.

MHA112 holds a unique premise to target hidden metastatic niches in LN. Thus, the effect of the LN delivery of MHA112 in the tumor population in the LN was investigated. The extent of MHA112's ability to restore the overall structure of LN was also investigated. Tumors are known to create a fibrotic environment. 4T1 tumor-draining lymph nodes (TDLNs) were cut by cryo-sectioning and stained with anti-HEV (sc-19602, SCBT), anti-LYVE1 (ab14917, Abcam), anti-Pan-Cytokeratin (C2931, Sigma), anti-collagen I (ab34710, Abcam), anti-collagen IV (ab6586, Abcam), and anti-laminin (ab11575, Abcam). DAPI (VECTASHIELD, Vector Laboratories) was used to counterstain the cell nuclei. The stained tissue sections were visualized using an EVOS™ FL Auto 2 Imaging System. The images in FIG. 8 show that TDLNs of control group and free Taxol group expanded in HEVs and lymphatic (LYVE1) areas. The expansion of HEVs and lymphatics in MHA112-Taxol TDLNs was less than other groups. Moreover, Pan-Cytokeratin indicated that primary tumor metastasis in TDLNs of MHA112-Taxol group was also significantly decreased, comparing to other groups. The structure changes of TDLNs was also examined. As it is shown in FIG. 9, collagen I, IV and laminin expression levels were lower in MHA112-Taxol. This data indicated that TDLNs fibrosis of MHA112-Taxol had been improved.

Figure 10:
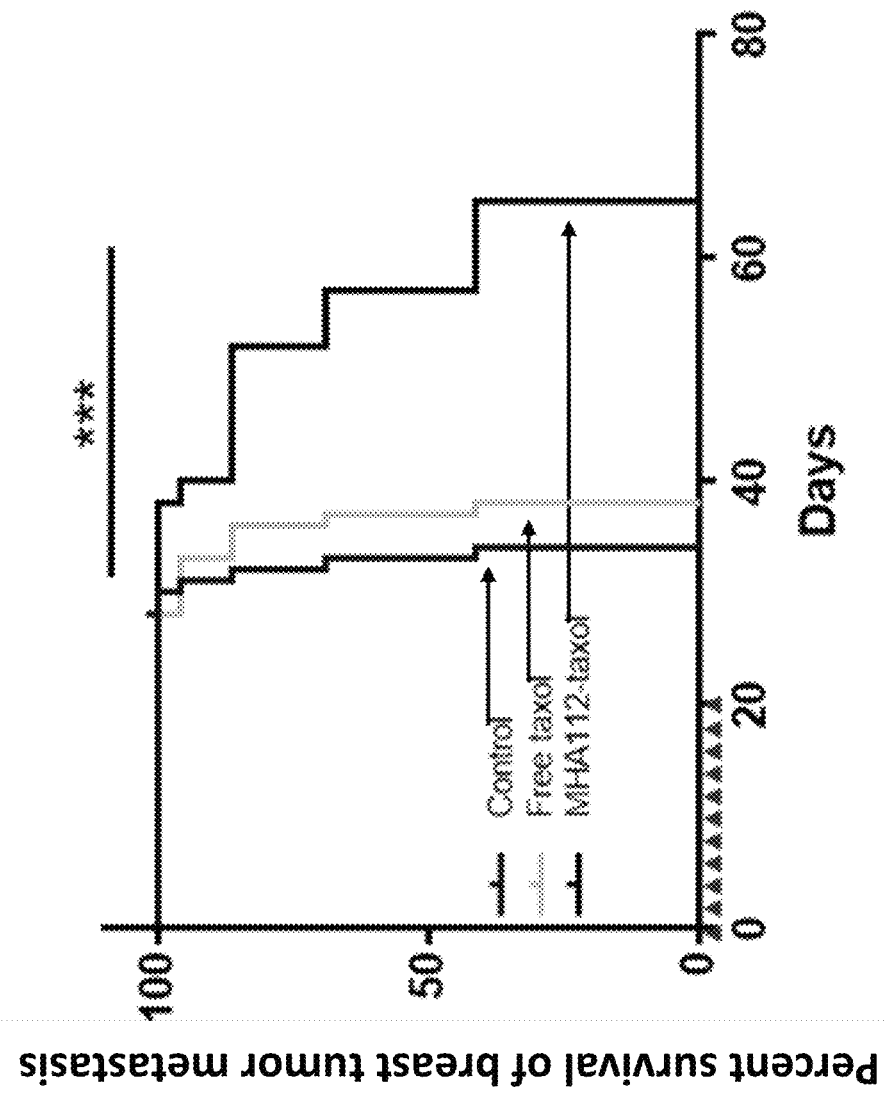
FIG. 10: Survival curve shows significantly longer survival of 4T1 breast tumor liver portal vein metastasis model that received MHA112-taxol (n=5) in comparison to the control and free taxol groups. ***P<0.001. Triangles represent injection days.

Example 8: MHA112-Drug Conjugation Increased Survival in In Vivo Metastatic Cancer Model To investigate the effect of MHA112-Taxol on tumor metastasis, 4T1 tumor cell lines were gently injected into the portal vein ($1 \times 10^4$ cells per mouse) of mouse liver. Starting 4 hours post-implantation, 160 ng of free Taxol or MHA112-taxol were administered every other day intraperitoneally for 20 days. Survival was monitored every day. The survival curve in FIG. 10 shows that the median survival time (MST) of the control group and the free Taxol group were 36 days and 37 days, respectively. The MST in the MHA112-Taxol group was significantly longer ($p<0.0001$), MST=58.

Figure 11:
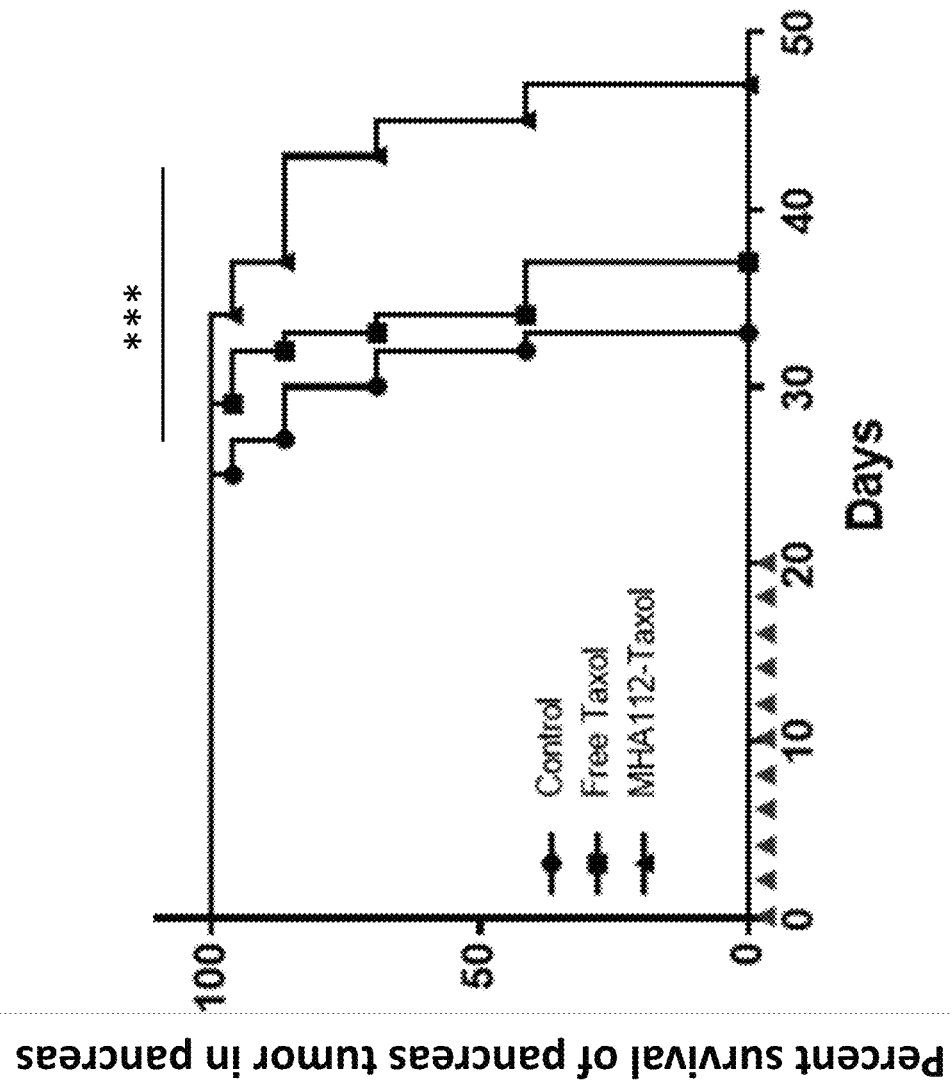
FIG. 11. Survival curve of panc02 pancreas tumors in pancreas showed significantly longer survival of MHA112-Taxol (n=5) than control and free Taxol (n=5). Triangles indicate the injection points. ***P<0.001

Example 9: MHA112-Drug Conjugation Increased Survival of Pan02 Pancreas Cancer Model Mice were anesthetized with isoflurane, and Panc02 pancreas tumor cells were gently injected in pancreas of mice. Two million cells ($2 \times 10^6$ cells) were injected per mouse for Panc02 tumor model. Starting 4 hours post-implantation, 160 ng of free Taxol or MHA112-taxol were administered every other day intraperitoneally for 20 days. Survival was monitored every day. The survival curve in FIG. 11 shows that the median survival time (MST) of the control group and the free Taxol group were 30 days and 32 days, respectively. The MST in the MHA112-Taxol group was significantly longer ($p<0.001$), MST=45.

Materials and Methods Used in Examples 7 to 9

Antibody-Drug Conjugates

Glutaric anhydride (100 mg, Sigma-Aldrich) and taxol (33 mg, LC laboratories) were prepared in a 4 mL vial dried under high vacuum for 24 hours and dissolved in 1 mL of pyridine. The solution was stirred at room temperature under Ar atmosphere for 2 hours. The reaction was quenched by removal of solvent under high vacuum for 2 hours. 2'-Glutaryl taxol was purified by a reversed phase HPLC (Phenomenex Luna 5 μm C18 250×10.0 mm, flow rate 2 mL/min, UV 250 nm detection) with a gradient solvent system (15% to 75% ACN/H2O with 0.1% formic acid for 40 minutes). 2'-glutaryl taxol (0.2 mg) dissolved in DMSO (Thermo Scientific Fisher) was activated with 1-ethyl-3-(3-dimethylaminopropyl)carbodiimide hydrochloride (EDC, 0.4 mg, Sigma-Aldrich) and Sulfo-NHS (N-hydroxysulfosuccinimide) (1.1 mg, Thermo Scientific Fisher) for 15 minutes at room temperature in MES buffer (pH 6.0, Thermo Scientific Fisher) (final solution; ~1 mL in 10% DMSO). The EDC was quenched by 2-mercaptoethanol (1.4 μL, Sigma-Aldrich) for 10 min. Immediately, the pH of solution increased by $Na_2CO_3$ (0.1 M, Sigma-Aldrich) to ~8. MHA112 dissolved in PBS (pH 7.4, Corning) was mixed with the activated 2'-glutaryl taxol at room temperature for 2 hours (1:20 molar ratio of MHA112 to taxol, final solution; 10% DMSO). Dialysis was given by a centrifugal filter (Amicon®, 10 kD MWCO, Sigma-Aldrich) at 10,000 rpm for 15 minutes with 2 times, to remove the free taxol. The solution further was purified by a desalting column (Zeba™, 7 kD MWCO, Thermo Scientific Fisher).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing tumor growth or metastasis of a peripheral lymph node addressin (PNAd)-expressing malignancy in a human subject in need thereof, the method comprising administering to the human subject a therapeutically effective amount of an anti-PNAd antibody, or PNAd-binding fragment thereof, wherein the anti-PNAd antibody or the PNAd-binding fragment thereof comprises:
   (a) a heavy chain variable region (VH), wherein the VH comprises a VH complementarity determining region 1 (CDR1) comprising the amino acid sequence of SEQ ID NO: 3, a VH CDR2 comprising the amino acid sequence of SEQ ID NO:4, and a VH CDR3 comprising the amino acid sequence of SEQ ID NO:5; and
   (b) a light chain variable region (VL), wherein the VL comprises a VL CDR1 comprising the amino acid sequence of SEQ ID NO:8, a VL CDR2 comprising the amino acid sequence of SEQ ID NO:9, and a VL CDR3 comprising the amino acid sequence of SEQ ID NO:10; wherein the anti-PNAd antibody, or PNAd-binding fragment thereof, is conjugated to a therapeutic agent, wherein the therapeutic agent is a checkpoint inhibitor or a chemotherapeutic agent.

2. The method of claim 1, wherein the PNAd-expressing malignancy is lymphoma, breast cancer, or pancreatic cancer.

3. The method of claim 1, wherein the chemotherapeutic agent is a cytotoxic agent.

4. The method of claim 1, wherein the chemotherapeutic agent is Taxol.

5. The method of claim 1, wherein the chemotherapeutic agent is Tacrolimus, mycophenolate mofetil, sirolimus, fingolimod, myriocin, cyclophosphamide, rapamycin, an anti-CD3 antibody, an anti-CD25 antibody, an anti-IL6 antibody, an anti-CTLA 4 antibody, adalimumab, or an anti-CD52 antibody.

6. The method of claim 3, wherein the chemotherapeutic agent is an antimetabolite, an alkylating agent, an anthracycline, an antibiotic, a cytotoxic agent, or an anti-mitotic agent.

7. The method of claim 6, wherein the cytotoxic agent is taxol, mitomycin, etoposide, tenoposide, vincristine, vinblastine, colchicin, doxorubicin, daunorubicin, mitoxantrone, mithramycin, actinomycin D, or puromycin.

8. The method of claim 6, wherein the antimetabolite is methotrexate, 6-mercaptopurine, 6-thioguanine, cytarabine, 5-fluorouracil dacarbazine.

9. The method of claim 6, wherein the alkylating agent is mechlorethamine, thiotepa, chlorambucil, melphalan, carmustine, lomustine, cyclothosphamide, busulfan, dibromomannitol, streptozotocin, mitomycin C, or cis-dichlorodiamine platinum (II) cisplatin.

10. The method of claim 6, wherein the anthracycline is daunorubicin or doxorubicin.

11. The method of claim 6, wherein the antibiotic is dactinomycin, bleomycin, mithramycin, or anthramycin.

12. The method of claim 6, wherein the anti-mitotic agent is vincristine or vinblastine.

13. The method of claim 2, wherein the PNAd-expressing malignancy is lymphoma.

14. The method of claim 2, wherein the PNAd-expressing malignancy is breast cancer.

15. The method of claim 2, wherein the PNAd-expressing malignancy is pancreatic cancer.

\* \* \* \* \*

SEQUENCE LISTING

```
<160> NUMBER OF SEQ ID NOS: 18

<210> SEQ ID NO 1
<211> LENGTH: 351
<212> TYPE: DNA
<213> ORGANISM: Artificial Sequence
<220> FEATURE:
<223> OTHER INFORMATION: Sequence encoding MHA112 Heavy Chain

<400> SEQUENCE: 1
caggtgcagc tgaaggagtc aggacctggc ctggtggcgc cctcacagag cctgtccatc        60
acttgcactg tctctgggtt ttcattaacc agctatggtg tagactgggt tcgccagcct       120
ccaggaaagg gtctggagtg gctgggagta atatgggtg gtggaagcac aaattataat       180
tcagctctca tgtccagact gagcatcagc aaagacaact ccaagagcca agttttctta       240
aaaatgaaca gtctgcaaac tgatgacaca gccatgtact actgtgccaa acatagtaaa       300
``` gggggggtact tcgatgtctg gggcacaggg accacggtca ccgtctcctc a       351

<210> SEQ ID NO 2
<211> LENGTH: 117
<212> TYPE: PRT
<213> ORGANISM: Artificial Sequence
<220> FEATURE:
<223> OTHER INFORMATION: MHA112 Heavy chain

<400> SEQUENCE: 2

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Asp Trp Val Arg Gln Pro Pro Gly Lys Gly Leu Glu Trp Leu
        35                  40                  45

Gly Val Ile Trp Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys His Ser Lys Gly Gly Tyr Phe Asp Val Trp Gly Thr Gly Thr Thr
            100                 105                 110

Val Thr Val Ser Ser
        115

<210> SEQ ID NO 3
<211> LENGTH: 7
<212> TYPE: PRT
<213> ORGANISM: Artificial Sequence
<220> FEATURE:
<223> OTHER INFORMATION: MHA112 Heavy chain CDR1

<400> SEQUENCE: 3

Gly Phe Ser Leu Thr Ser Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: MHA112 Heavy chain CDR2

<400> SEQUENCE: 4

Trp Gly Gly Gly Ser
1               5

<210> SEQ ID NO 5
<211> LENGTH: 9
<212> TYPE: PRT
<213> ORGANISM: Artificial Sequence
<220> FEATURE:
<223> OTHER INFORMATION: MHA112 Heavy chain CDR3

<400> SEQUENCE: 5

His Ser Lys Gly Gly Tyr Phe Asp Val
1               5

<210> SEQ ID NO 6
<211> LENGTH: 318

```
<212> TYPE: DNA
<213> ORGANISM: Artificial Sequence
<220> FEATURE:
<223> OTHER INFORMATION: Sequence encoding MHA112 light Chain

<400> SEQUENCE: 6
gaaattgtgc tcactcagtc tccagccatc acagctgcat ctctggggca aaaggtcacc    60
atcacctgca gtgccagctc aagtgtaagt tacatgcact ggtaccagca gaagtcaggc   120
acctccccca aaccatggat ttatgaaata tccaaactgg cttctggagt cccagctcgc   180
ttcagtggca gtgggtctgg gacctcttac tctctcacaa tcagcagcat ggaggctgaa   240
gatgctgcca tttattactg ccagcagtgg aattatcctc ttatcacgtt cggtgctggg   300
accaagctgg agctgaaa                                                 318

<210> SEQ ID NO 7
<211> LENGTH: 106
<212> TYPE: PRT
<213> ORGANISM: Artificial Sequence
<220> FEATURE:
<223> OTHER INFORMATION: MHA112 Light chain

<400> SEQUENCE: 7

Glu Ile Val Leu Thr Gln Ser Pro Ala Ile Thr Ala Ala Ser Leu Gly
1               5                  10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ala Gly Thr Lys Leu Glu Leu Lys
            100                 105

<210> SEQ ID NO 8
<211> LENGTH: 10
<212> TYPE: PRT
<213> ORGANISM: Artificial Sequence
<220> FEATURE:
<223> OTHER INFORMATION: MHA112 Light chain CDR1

<400> SEQUENCE: 8

Ser Ala Ser Ser Ser Val Ser Tyr Met His
1               5                  10

<210> SEQ ID NO 9
<211> LENGTH: 7
<212> TYPE: PRT
<213> ORGANISM: Artificial Sequence
<220> FEATURE:
<223> OTHER INFORMATION: MHA112 Light chain CDR2

<400> SEQUENCE: 9

Glu Ile Ser Lys Leu Ala Ser
1               5

<210> SEQ ID NO 10
<211> LENGTH: 9
```

-continued

<212> TYPE: PRT
<213> ORGANISM: Artificial Sequence
<220> FEATURE:
<223> OTHER INFORMATION: MHA112 Light chain CDR3

<400> SEQUENCE: 10

Gln Gln Trp Asn Tyr Pro Leu Ile Thr
1               5

<210> SEQ ID NO 11
<211> LENGTH: 25
<212> TYPE: PRT
<213> ORGANISM: Artificial Sequence
<220> FEATURE:
<223> OTHER INFORMATION: MHA112 Heavy chain framework region 1

<400> SEQUENCE: 11

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 12
<211> LENGTH: 19
<212> TYPE: PRT
<213> ORGANISM: Artificial Sequence
<220> FEATURE:
<223> OTHER INFORMATION: MHA112 Heavy chain framework region 2

<400> SEQUENCE: 12

Gly Val Asp Trp Val Arg Gln Pro Pro Gly Lys Gly Leu Glu Trp Leu
1               5                   10                  15

Gly Val Ile

<210> SEQ ID NO 13
<211> LENGTH: 41
<212> TYPE: PRT
<213> ORGANISM: Artificial Sequence
<220> FEATURE:
<223> OTHER INFORMATION: MHA112 Heavy chain framework region 3

<400> SEQUENCE: 13

Thr Asn Tyr Asn Ser Ala Leu Met Ser Arg Leu Ser Ile Ser Lys Asp
1               5                   10                  15

Asn Ser Lys Ser Gln Val Phe Leu Lys Met Asn Ser Leu Gln Thr Asp
            20                  25                  30

Asp Thr Ala Met Tyr Tyr Cys Ala Lys
        35                  40

<210> SEQ ID NO 14
<211> LENGTH: 11
<212> TYPE: PRT
<213> ORGANISM: Artificial Sequence
<220> FEATURE:
<223> OTHER INFORMATION: MHA112 Heavy chain framework

<400> SEQUENCE: 14

Trp Gly Thr Gly Thr Thr Val Thr Val Ser Ser
1               5                   10

<210> SEQ ID NO 15
<211> LENGTH: 23
<212> TYPE: PRT
<213> ORGANISM: Artificial Sequence
<220> FEATURE:

```
<223> OTHER INFORMATION: MHA112 Light chain framework region 1

<400> SEQUENCE: 15

Glu Ile Val Leu Thr Gln Ser Pro Ala Ile Thr Ala Ala Ser Leu Gly
1               5                   10                  15

Gln Lys Val Thr Ile Thr Cys
            20

<210> SEQ ID NO 16
<211> LENGTH: 15
<212> TYPE: PRT
<213> ORGANISM: Artificial Sequence
<220> FEATURE:
<223> OTHER INFORMATION: MHA112 Light chain framework region 2

<400> SEQUENCE: 16

Trp Tyr Gln Gln Lys Ser Gly Thr Ser Pro Lys Pro Trp Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: MHA112 Light chain framework region 3

<400> SEQUENCE: 17

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Ile Tyr Tyr Cys
            20                  25                  30

<210> SEQ ID NO 18
<211> LENGTH: 10
<212> TYPE: PRT
<213> ORGANISM: Artificial Sequence
<220> FEATURE:
<223> OTHER INFORMATION: MHA112 Light chain framework region 4

<400> SEQUENCE: 18

Phe Gly Ala Gly Thr Lys Leu Glu Leu Lys
1               5                   10
```